United States Patent
Vidal Fayos et al.

(10) Patent No.: US 10,850,022 B2
(45) Date of Patent: Dec. 1, 2020

(54) SEPARATING AND TRANSFERRING PHASES OF A FLUID THROUGH CENTRIFUGATION

(71) Applicant: NTE-SENER HEALTHCARE, S.A., Cerdanyola del Vallès (ES)

(72) Inventors: Francisco Vidal Fayos, Mataró (ES); Nuria Noguera Ferrer, Barcelona (ES); Emiliano Tolosa González, Barcelona (ES)

(73) Assignee: NTE-SENER HEALTHCARE, S.A., Cerdanyola del Vallès (ES)

(*) Notice: Subject to any disclaimer, the term of this patent is extended or adjusted under 35 U.S.C. 154(b) by 499 days.

(21) Appl. No.: 15/569,752

(22) PCT Filed: Apr. 28, 2016

(86) PCT No.: PCT/EP2016/059570
§ 371 (c)(1),
(2) Date: Oct. 26, 2017

(87) PCT Pub. No.: WO2016/174180
PCT Pub. Date: Nov. 3, 2016

(65) Prior Publication Data
US 2018/0147340 A1 May 31, 2018

(30) Foreign Application Priority Data
Apr. 29, 2015 (EP) .................................. 15382215

(51) Int. Cl.
*A61M 1/36* (2006.01)
*A61M 1/02* (2006.01)
*B04B 5/04* (2006.01)

(52) U.S. Cl.
CPC ........ *A61M 1/3696* (2014.02); *A61M 1/0209* (2013.01); *A61M 1/3693* (2013.01);
(Continued)

(58) Field of Classification Search
CPC .............. A61M 1/0209; A61M 1/3693; A61M 1/3696; A61M 2202/0423; B04B 5/0407;
(Continued)

(56) References Cited

U.S. PATENT DOCUMENTS 4,177,921 A 12/1979 Nielsen
4,416,778 A * 11/1983 Rogers .................. A61K 35/14
210/516

(Continued)

OTHER PUBLICATIONS

Invitation to Pay Additional Fees and, Where Applicable, Protest Fee of the International Searching Authority (and partial search report) dated Jul. 1, 2016 for PCT/EP2016/059570, 8 pages.

(Continued)

*Primary Examiner* — Timothy C Cleveland
(74) *Attorney, Agent, or Firm* — Squire Patton Boggs (US) LLP

(57) ABSTRACT

A system for separating and transferring phases of a fluid through centrifugation including a centrifuge having a rotating axis, a platform that is rotatable around the rotating axis; and a device for separating and transferring the phases of the fluid. The device includes a separating container and a receiving container connected to the separating container through a connecting channel. A passive valve system is provided in the connecting channel. The device is mounted in the centrifuge platform such that in use at a first predefined range of centrifugal force a fluid provided within the separating container is separated into phases and at a second predefined range of centrifugal force the valve system opens, thereby transferring a phase of the fluid from the separating container to the receiving container.

14 Claims, 11 Drawing Sheets

(52) U.S. Cl.
CPC .......... *B04B 5/0407* (2013.01); *B04B 5/0428* (2013.01); *B04B 5/0442* (2013.01); *A61M 2202/0423* (2013.01)

(58) Field of Classification Search
CPC ................ B04B 5/0428; B04B 5/0442; B04B 2005/0485
See application file for complete search history.

(56) References Cited

U.S. PATENT DOCUMENTS

| | | |
|---|---|---|
| 4,447,220 A | 5/1984 | Eberle |
| 2004/0217069 A1 | 11/2004 | Columbus |
| 2005/0184012 A1 | 8/2005 | Coull et al. |
| 2014/0234183 A1 | 8/2014 | Kolenbrander et al. |

OTHER PUBLICATIONS

International Search Report and Written Opinion of the International Searching Authority dated Aug. 29, 2016 for PCT/EP2016/059570, 21 pages.

* cited by examiner

SEPARATING AND TRANSFERRING PHASES OF A FLUID THROUGH CENTRIFUGATION

This application claims the benefit of European Patent Application 15382215.0 filed on Apr. 29, 2015.

The present disclosure relates to systems and methods for separating and transferring phases of a fluid through centrifugation, in particular for biological fluids such as blood and/or blood derivatives' components.

BACKGROUND

The repair and regeneration of all or part of organs and tissues is a common process that occurs in response to multiple pathologies such as trauma, ischemia, acute and chronic inflammation and degenerative processes. It is known that peripheral blood is fully involved in any hemostatic, inflammatory, reparative and regenerative process.

It is further known that blood consists of many components, namely red blood cells (RBC), white blood cells (WBC), platelets and plasma, and that peripheral blood cells including RBC, platelets and WBC have a central role in regenerative and reparative activity. Modern regenerative therapies are thus largely dependent on the use of the different blood components.

In that sense, it is known that blood spontaneously sediments into layers of components having different densities under the influence of gravity. Alternatively centrifugal force can be used to somehow speed up blood decanting into phases. And that a whole blood unit that is collected from a donor can thus be processed to separate it into its components, each component then being able to be transfused to a patient for a different therapy.

Centrifugation is a well-known technique for separating blood into its individual components. Components having the highest density thus concentrate in a section of the container that is most distant from an axis of rotation of the centrifuge, whereas the lowest density component is packed in a layer the closest to the axis of rotation.

For example, when blood with an anticoagulant is subjected to centrifugal force during a certain time, RBC which have the highest density thus concentrate in the section of the container that is most distant from the axis of rotation of the centrifuge.

WBC which have the second highest density are thus concentrated in a layer supported by the RBC layer that is closer to the axis of rotation of the centrifuge. Platelets with a density slightly lower than that of the WBC are grouped in a layer next to the WBC layer, closer to the axis of rotation. And plasma with the lowest density is packed in a layer the closest to the axis of rotation.

And when e.g. whole blood is processed in a centrifuge in the absence of any anticoagulant, three main different phases may be separated. First a red cell layer with the highest density disposed at the section of the container that is most distant from the axis of rotation of the centrifuge, then a rigid and elastic platelet-rich fibrin (PRF) gel with a density that is lower than that of the red cell layer and that is supported by the red cell layer, and finally a liquid supernatant serum which is packed in a layer the closest to the axis of rotation of the centrifuge.

Depending on the rotational speed of the centrifuge and the centrifuging time, anticoagulated blood can thus be separated into more or less layers. In an example, WBC are mixed with platelets in a layer called "buffy coat". And at lower centrifugation speed, blood may be separated into two layers, RBC and platelets rich plasma (PRP). By constant rotation of the centrifuge, a sharp distinct edge can be maintained at the boundary of the separated layers, e.g. the separated RBC layer and PRP layer. And such an edge can rapidly be disintegrated when the centrifuge is stopped.

In order to prevent contamination between blood phases it is also known to transfer one or more of the phases during centrifugation as the separating lines between phases remain very sharp under centrifugal forces.

Therefore, current blood separation techniques tend to maintain the centrifuge spinning during extraction of the phases in order to avoid or at least minimize remixing of the blood phases once the centrifuge is stopped. In that sense, it is known to activate extracting means such as motors, hydraulic means or similar during centrifugation in order to extract blood phases having different densities. However, these systems normally require special centrifuges or centrifuge housings adapted to comprise or at least be able to activate the extracting means. Also extra energy is normally required to provide the required power to the extracting means or to the electrical actuators normally used to control open and close functions of the valves forming part of the extracting. Document U.S. Pat. No. 4,447,220 describes such systems.

Document US2004217069 discloses a rotor assembly for the collection, separation and sampling of rare blood cells in which a displacing fluid reservoir is located at least partially radially inward of a centrifuging chamber, wherein a displacing fluid of a greater density than the fluid in the centrifuging chamber is retained in the displacing fluid reservoir. And upon rotation of the rotor assembly, the displacing fluid is allowed to pass into the centrifuging chamber.

Document US2005184012 describes a fluid concentrator including a main housing defining a centrifuging chamber that also holds a filter.

Document U.S. Pat. No. 4,177,921 discloses a multi-compartment rotor liner having an annular chamber surrounding a central chamber in which a material (chyle material) is collected during centrifugation.

Document US2014234183 discloses a disposable blood separation set and a centrifugal blood processing system comprising a blood processing chamber adapted to be mounted on a rotor of a centrifuge.

There is thus a need for alternative systems able to separate and transfer phases of a fluid during centrifugation which are cost-effective and can also guarantee a safe extraction, i.e. in a sterile environment, and without human manipulation.

SUMMARY

In a first aspect, the disclosure provides a system for separating and transferring phases of a fluid through centrifugation. The system comprises a centrifuge having a rotating axis, a platform that is rotatable around the rotating axis, and a device for separating and transferring the phases of the fluid. The device comprises a separating container having a receiving end configured to receive the fluid and a receiving container arranged in fluid communication with the separating container through a connecting channel. The device further comprises a passive valve system provided in the connecting channel, wherein the device is mounted in the centrifuge platform with the separating and the receiving containers arranged side by side and with a longitudinal axis of each container substantially perpendicular to the rotating axis of the centrifuge such that in use at a first predefined range of centrifugal force a fluid provided within the separating container is separated into phases and at a second predefined centrifugal force range the passive valve system opens thereby transferring a phase of the fluid from the separating container to the receiving container.

Throughout the present description and claims a passive valve system is to be understood as a valve system which does not require external energy sources such as manual electromechanical devices and/or electric actuators, but only uses existing forces such as the centrifugal force generated by the rotation of the centrifuge.

According to this aspect, during rotation of the centrifuge at certain rotational speeds the centrifugal forces generated produce the separation into phases of a fluid provided within any of the containers. Furthermore, at another certain rotational speeds, e.g. the rotational speeds that generate the second predefined centrifugal force range, the pressure difference between an inside of the separating container and an inside of the receiving container is such that the passive valve system opens thereby transferring a phase of the fluid from the separating container to the receiving container. Although a relatively precise design of the device may be required such that the passive valve system opens at the predefined centrifugal force range, the use of the device is quite simple, even for relatively unskilled personnel. Furthermore as there is no exposure of the fluid with the outside, a safe transfer is guarantee. And the opening of the valve system is done without providing extra energy to actuate the valve and without human manipulation.

Further according to this aspect, the system is configured such that in use, a phase of the fluid having the highest density is packed in a layer in a section of the separating container that is most distant from the rotating axis of the centrifuge whereas less dense phases accumulate at zones in the separating container progressively closer to the rotating axis. And the phase of the fluid having the lowest density is packed in a layer the closest to the rotating axis.

It should be noted that a predefined range of centrifugal force able to open a passive valve system depends on various design parameters such as the type of valve, the geometry of the containers, the presence or not of plungers and/or weights, the density of the fluid to be separated, the distance of the valves to the rotating axis of the centrifuge and/or combinations thereof.

In some examples, the connecting channel may be coupled to the separating container at a point such that 30-50% of a total volume of the separating container is left more distant from the centrifuge rotating axis than the channel itself such that in use, when the second predefined range of centrifugal force is reached, a phase of the fluid being left closer from the centrifuge rotating axis than the channel may flow through the channel to the receiving container. In these examples, the portion of the fluid provided at 70-50% of the total volume of the separating container that is left closer to the centrifuge rotating axis than the channel may be transferred to the receiving container. In some of these examples, the fluid may be blood or blood derivatives.

Throughout the present description and claims blood and blood derivatives is to be understood as any composition selected from the group consisting of whole blood, a platelet-rich plasma, a platelet concentrate, a leukocyte-rich plasma, a leukocyte concentrate, a platelet-poor plasma, a plasma concentrate and mixtures or combinations thereof.

In other words, the connecting channel may be coupled to the separating container at a coupling position such that a portion of the fluid (blood in an example) held in the container may be left on each side (i.e. closer/more distant from the centrifuge rotating axis) of the channel. Since the density of the phases of a fluid is normally higher in the direction of the centrifugal force, the portion of the separating container that is left closer to the rotating axis will house the phase having the lowest density whereas the portion of the separating container that is left more distant to the rotating axis will house the phase having the highest density.

Alternatively, in the device design phase, it may be possible to substantially establish the point within the separating container in which a borderline of two phases of a fluid will be created during centrifugation. The coupling of the connecting channel to the separating container may thus be established substantially closer to the rotating axis than such a borderline or more distant from the borderline depending on circumstances. In some cases it may be desirable to separate the entire phase that is left closer to the rotating axis, in these cases, the connecting channel may be coupled substantially more distant than the borderline so that the entire phase can be transferred to the receiving container. In these cases, a certain "contamination" of phases may be allowed and more fluid phase, even the entire phase, can be transferred.

In some examples, the system may further comprise a further separating container having a receiving end, a further receiving container arranged in fluid communication with the further separating container through a further connecting channel, and a further passive valve system provided at the further connecting channel. The passive valve systems may open within substantially the same second predefined range of centrifugal force, and the connecting channels may be respectively connected to the separating and receiving containers at a distal end thereof with respect to the centrifuge rotating axis such that in use within the first predefined range of centrifugal force phases of a fluid provided within each separating container may be separated and within the second predefined centrifugal force range the valve systems may open thereby transferring a phase of the fluid distally housed within each separating container to each respective receiving container. In these examples, a phase of the fluid housed within the separating containers that may be left distally arranged with respect to the rotating axis may have the highest density.

In some examples, the system may further comprise a separating connecting channel connecting the distal ends of the separating containers and a separating passive valve system provided in the separating connecting channel, wherein the separating passive valve system may open at a third predefined centrifugal force range, the third predefined centrifugal force range may be higher than the second predefined centrifugal force range required for opening the passive valve systems.

In some examples, one or more separating containers may further comprise a weight at the receiving ends. The weight may be displaceable in a direction of the centrifugal force generated in use by rotation of the centrifuge. The weight thus aids the centrifugal force and contributes creating a pressure difference at the passive valve systems and accelerating displacement of the transferred fluid phase. In some of these examples, one or more receiving containers may comprise another displaceable weight.

In some of these examples, one or more weights may comprise a plunger reciprocally movable inside the respective container lengthwise, in a direction of the centrifugal force generated in use by rotation of the centrifuge. In these cases, the plunger may comprise a filling and extracting valve. In these cases, extracting of the final product may be done through the filling and extracting valve by pushing the plunger in a direction of a longitudinal axis of the container so as to cause the fluid held in the container to be pushed up into a further container that may be provided in the filling and extracting valve.

In some of these examples, the plunger may extend from an outside end to an inside end, the inside end in use faces an inside of the container. In these cases, the inside end may be provided with one or more projections and/or grooves or combinations thereof. Alternatively, channels may be foreseen. This way, when the plunger is pushed towards the fluid, in the direction of the longitudinal axis of the container, the fluid runs through the grooves or channels in its way towards the exit (the filling and extracting valve). The provision of grooves thus enhances fluid removal through the extracting valve by dispersing the fluid between the grooves or channels and the extracting valve. This reduces potentially tamponade or blockage of the extracting valve due to excess of fluid trying to exit at the same time.

Inventors have found that the provision of grooves or channels and projections lead to particularly good results when the system is used for separating and transferring phases of a fluid in which the fluid phase immediately next to the phase that is to be extracted is a solid or semi-solid phase, including e.g. a gelatinous mass such as blood clots.

In examples, when a fluid is separated into phases inside the container, once a fluid phase is already extracted through the extracting valve, the projections provided at the inside end of the container may push further (squeeze) towards the immediately next phase of the fluid. This way, a portion of the fluid phase that was extracted and that may be mixed with the immediately next phase can be extracted further from this immediately next phase thus increasing the amount of fluid phase that may be obtained.

In some examples one or more separating containers may be mounted in the centrifuge platform at a different distance to the rotating axis than the receiving containers thereby contributing to create a pressure difference at the passive valve systems.

In a further aspect, a device for a system substantially as hereinbefore described may be provided. The device may comprise a separating container having a receiving end configured to receive the fluid, a receiving container arranged in fluid communication with the separating container through a connecting channel, and a passive valve system provided in the connecting channel. The device may be configured to be mounted in a centrifuge platform with the separating and the receiving containers arranged side by side and with a longitudinal axis of each container substantially perpendicular to a centrifuge rotating axis such that in use at a first predefined centrifugal force range a fluid provided within the separating container may be separated into phases and at a second predefined centrifugal force range the passive valve system may be opened thereby transferring a phase of the fluid from the separating container to the receiving container. In this device the connecting channel may be coupled to the separating container at a point such that 30-50% of a total volume of the separating container may be left more distant from the centrifuge rotating axis than the channel itself such that in use, when the second predefined range of centrifugal force is reached, the valve system is opened thereby transferring a phase of the fluid from the separating container to the receiving container through the channel. In this device the phase of the fluid being transferred corresponds to the phase being left closer from the centrifuge rotating axis than the connecting channel. This means that the phase of the fluid having the lowest density can be transferred from the separating container to the receiving container.

In still a further aspect, a further device for a system substantially as hereinbefore described may be provided. The device may comprise two separating containers each having a receiving end configured to receive a fluid, two receiving containers, each arranged in fluid communication with one separating container through a connecting channel, a passive valve system provided in each connecting channel, wherein the passive valve systems may open within the same second predefined range of centrifugal force. The device may be configured to be mounted in a centrifuge platform with the separating and the receiving containers arranged side by side and with a longitudinal axis of each container substantially perpendicular to a centrifuge rotating axis such that in use at a first predefined centrifugal force range a fluid provided within the separating containers may be separated into phases and at the second predefined centrifugal force range the passive valve systems may be opened thereby transferring a phase of the fluid from each separating container to the respective receiving container, wherein the connecting channels may be respectively connected to the containers at a distal end thereof with respect to the centrifuge rotating axis such that in use a phase of the fluid distally housed within each separating container may be transferred to each respective receiving container. The device may further comprise a separating connecting channel connecting the distal ends of the separating containers, and a separating passive valve system may be provided in the separating connecting channel. The separating passive valve system may open at a third predefined centrifugal force range, the third predefined centrifugal force range may be higher than the second predefined centrifugal force range required for opening the passive valve systems.

In some examples, the receiving end may be proximally arranged with respect to the rotating axis.

In some examples, the separating container may be rigid. In some of these cases, the receiving container may be a flexible bag. In other cases, the receiving container may also be a rigid container. In further examples, the separating container and the receiving container may both be flexible bags. In those cases involving one or more flexible bags the device may further comprise a rigid holder configured to receive the flexible containers and/or the connecting channel.

In the examples using flexible bags, the bags may be made of any suitable plastic material compatible with biological fluids and able to withstand high centrifugal forces, e.g. a PVC polymer.

In some examples, the connecting channel may be rigid. In others, it may be flexible.

In some examples the passive valve systems may be a closure membrane, a check valve or a cut off valve.

In those cases having a flexible connecting channel the passive valve system may further be a pinch valve.

In yet a still further aspect, a method of obtaining a product made of combining phases of a fluid may be provided. The method may comprise:
  filling a separating container with a fluid,
  filling a receiving container with a fluid, wherein the receiving container may be arranged in fluid communication with the separating container through a connecting channel, the connecting channel may comprise a passive valve system configured to open at a predefined centrifugal force range, introducing the containers and the connecting channel into a centrifuge platform such that the separating and receiving containers may be arranged side by side and with a longitudinal axis of each container substantially perpendicular to a centrifuge rotating axis, rotating the centrifuge platform at a first centrifugal speed range so as to obtain a first predefined centrifugal force range and during a first period of time to perform separation into phases of a fluid provided within the containers, rotating the centrifuge at a second centrifugal speed range so as to reach a second predefined centrifugal force range able to open the passive valve system thereby transferring a phase of the fluid from the separating container to the receiving container, rotating the centrifuge at a third centrifugal speed range so as to obtain a third centrifugal force range and during a second period of time so as to obtain separation into two phases of a fluid mixture housed within the receiving container, stopping the centrifuge, and extracting a product made of combining phases of the fluid mixture housed in the receiving container that may be consolidated at a layer the closest to the centrifuge rotating axis.

In some examples, the fluid provided in the receiving container and in the separating container may be substantially the same. In further examples, one or more additives may be added to at least one of the fluids provided in any of the separating or receiving containers. In more examples, different additives may be added to the fluids provided in the separating and receiving containers. In still more examples, different fluids with or without the same or different additives, may be provided in the separating and receiving containers. Other fluid combinations may also be foreseen.

BRIEF DESCRIPTION OF THE DRAWINGS

Non-limiting examples of the present disclosure will be described in the following with reference to the appended drawings, in which.

DETAILED DESCRIPTION OF EXAMPLES

Figure 1:
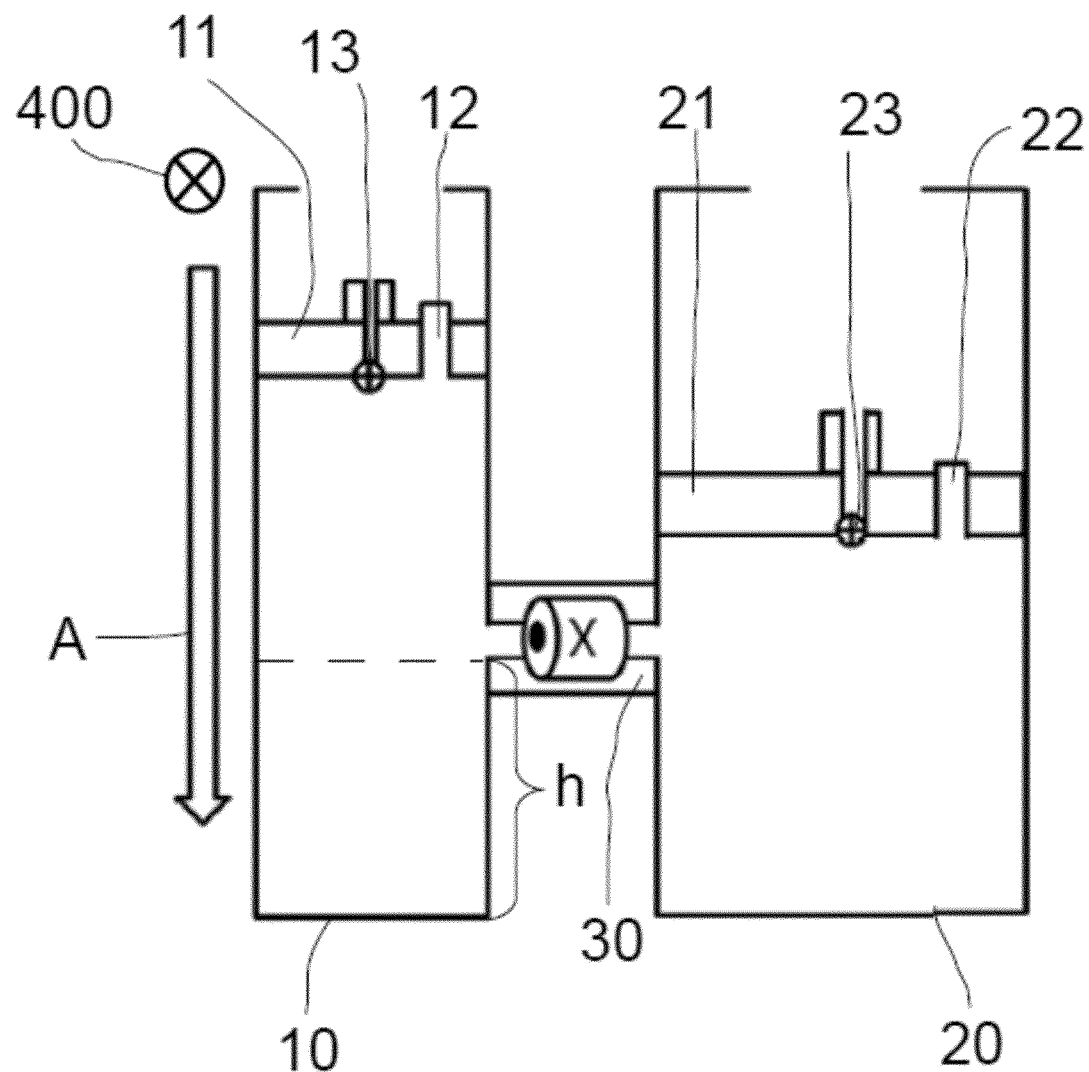
FIG. 1 shows an example of a device for separating and transferring phases of a fluid.

FIG. 1 shows a device for separating and transferring phases of a fluid according to an example. The device may comprise two rigid containers 10, 20. Container 10 may be a separating container and container 20 may be a receiving container. The containers 10, 20 may be in fluid communication through a rigid connecting channel 30 that may be provided with a check valve X that may in turn be calibrated to open within a predefined cracking pressure. In alternative cases, rigid containers may be connected via a flexible tube.

Throughout the present description and claims a check valve is to be understood as a non-return valve that works automatically, i.e. not controlled by a person or any external control and does not require external energy sources such as manual electromechanical devices and/or electric actuators. Typically a check valve is designed for a specific cracking pressure which is the minimum upstream pressure at which the valve will operate (open).

In that sense, the cracking pressure of a check valve is to be understood as a design parameter that contributes to the determination of the centrifugal force range at which the pressure difference at both ends of the valve opens the valve.

In further alternative examples, instead of check valves other passive valve systems may be foreseen such as e.g. a closure membrane or a cut off valve.

In the example of FIG. 1, the connecting channel 30 may be coupled to the separating container 10 at a height h such that a portion of the total volume of the container 10 may be left at each side of the connecting channel 30. This height may depend on the fluid to be separated into phases. In an example, the fluid may e.g. be blood and the point at which the connecting channel may be coupled to the separating container may be such that 30-50% of the total volume of the separating container may be left more distant from a rotating axis 400 (of the centrifuge platform in which the device is designed to be inserted) than the channel 30.

A plunger 11, 21 may further be provided at each container 10, 20 to guarantee isolation from the outside. In some of these cases, one or more weights may further be provided in one or more plungers. The plungers and weights contribute to generating the pressure difference required, in use, i.e. when the device is mounted within a centrifuge platform and rotation of the platform is turned on, for opening the passive valve system. The weight(s) may be mounted in the containers so as to be displaceable in a direction substantially coincident with a centrifugal force that is generated in use (arrow A).

In addition, the containers may comprise an air filter 12, 22 allowing the passage of air from inside the containers. In some cases, the filters may be waterproof allowing the passage of air, but not particles over a certain size depending on circumstances. In those cases containers comprising one or more plungers 11, 21 as shown in FIG. 1, the air filters 12, 22 may be provided at the plungers 11, 21.

The provision of air filters and/or plungers contributes towards preserving sterility of the system. The air filters may further be used for emptying air from inside the containers when filling the containers.

Furthermore, each container may be provided with a filling/extracting valve 13, 23 to maintain sterility of the container. In some cases, the filling/extracting valve may be a non-return valve. In those cases comprising one or more plungers 11, 21 as shown in FIG. 1, the filling/extracting valve 13, 23 may also be provided at the plungers 11, 21.

Figure 2:
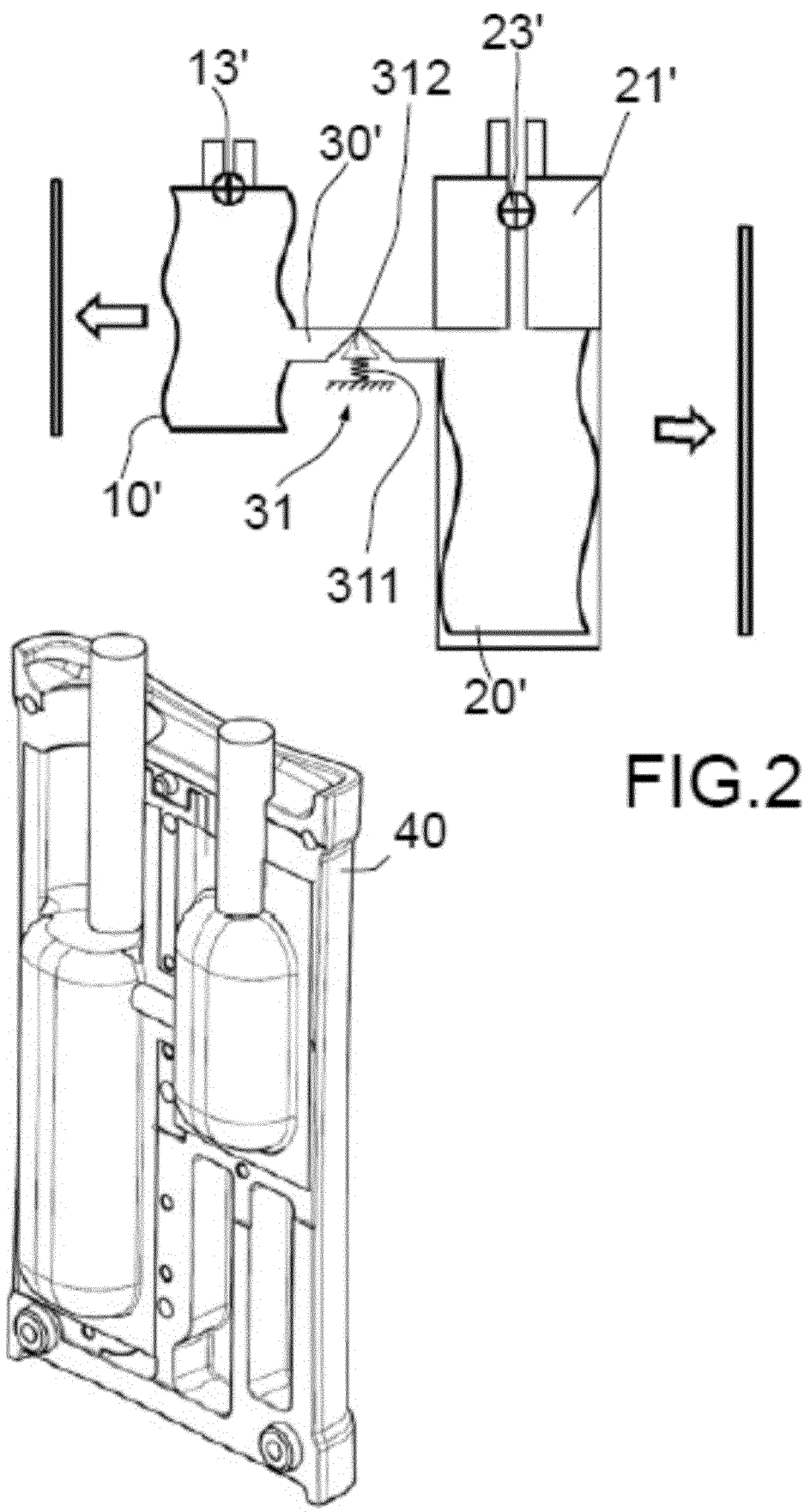
FIG. 2 shows another example of a device for separating and transferring phases of a fluid.

The example of FIG. 2 differs from that of FIG. 1 in that the containers 10', 20' may be flexible bags and the connecting channel 30' may be a flexible tube. In further examples, flexible containers may be connected via a rigid tube. In this example, the connecting channel 30' may comprise a pinch valve 31. The pinch valve 31 may comprise e.g. a spring 311 configured to be fixed to e.g. a holder 40 and a mass 312 able to push the spring 311 at a certain centrifugal force range generated in use. An aspect of using bags is that they are flat when they are empty so they require less storage space when they are empty.

In further alternatives, one container may be rigid and the other may be a flexible bag and the connecting channel may be flexible or rigid. In further examples, instead of a pinch valve other passive valve systems may be foreseen such as e.g. a closure membrane, a check valve or a cut off valve.

In the example of FIG. 2, a holder 40 may be provided. The holder 40 may be configured to receive the flexible bags (containers 10', 20') and the channel 30' so as to provide a frame defining a coupling of the connecting channel substantially similar to that explained in connection with FIG. 1. This means a coupling leaving a portion of the total volume at one side of the channel and another portion of the total volume at the other side of the channel.

In the example of FIG. 2, the separating container 10' may comprise a filling valve 13' and the receiving container 20' may comprise a plunger 21' with a filling/extracting valve 23'. In further alternatives, air filters may be provided substantially as described in connection with FIG. 1. In yet further examples, a plunger may further be provided in the separating container. And in more examples, no plunger may be provided at the receiving container.

Figure 3:
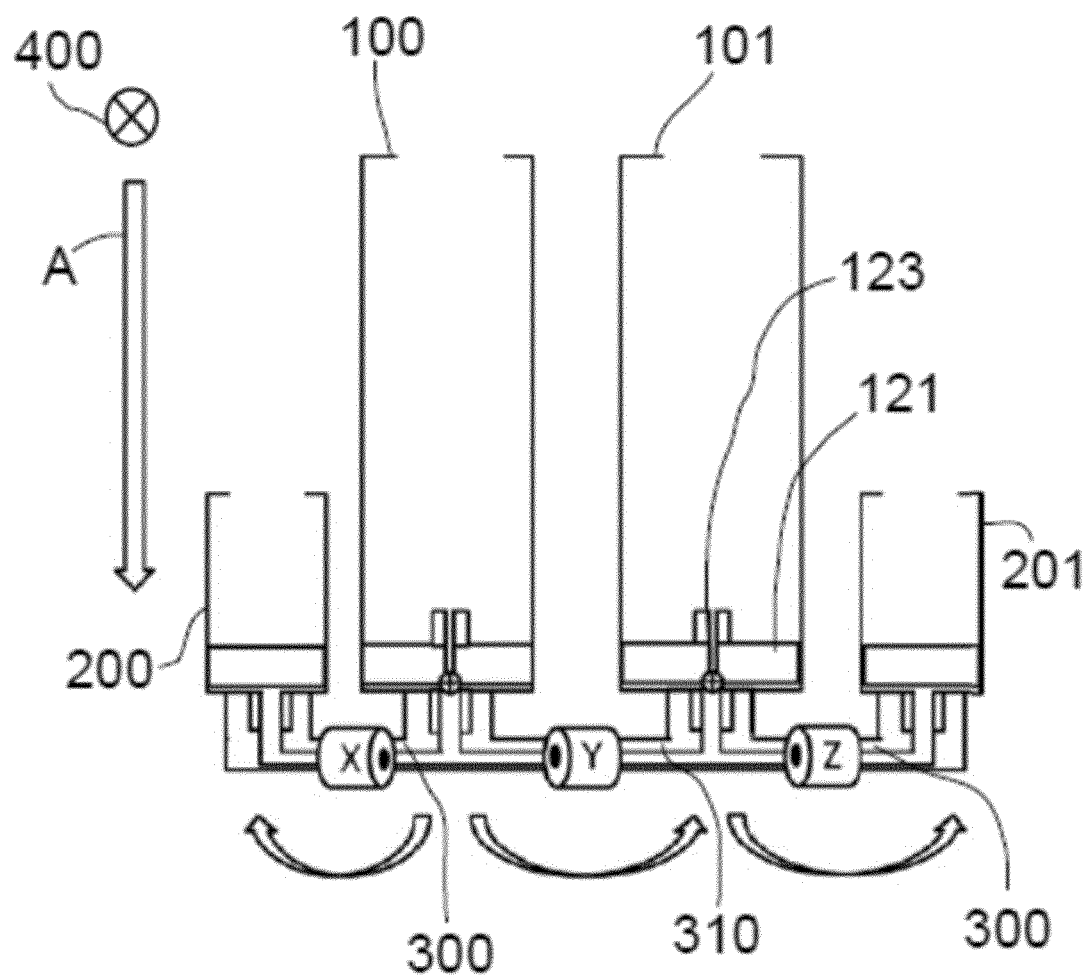
FIG. 3 shows a further example of a device for separating and transferring phases of a fluid.

The example of FIG. 3 shows a device that may comprise two separating containers 100 and 101 and two receiving containers 200 and 201. Each separating container 100, 101 may be fluidly connected to a receiving container 200, 201 by a connecting channel 300 that may comprise a check valve X, Z. Other valve systems or combinations of valve systems substantially as mentioned above may also be foreseen. Check valves X, Z may be calibrated to open at a cracking pressure such that in use and in combination with the other design parameters they open within the same centrifugal force range. Furthermore, one or more weights displaceable in the direction of the centrifugal force (arrow A) may be provided inside the separating containers in order to aid (contribute) creating the required pressure difference able to open the valves.

In the example of FIG. 3, all containers 100, 101, 200, 201 may be rigid containers. A plunger may further be provided inside one or more containers as explained in connection with FIG. 1. Flexible bags may also be foreseen as long as they are configured to be housed within a holder substantially as described in connection with the example of FIG. 2. In alternative examples, the separating containers may be rigid containers and the receiving containers may be flexible bags. Other combinations may also be foreseen depending on circumstances.

In the example of FIG. 3 a further fluid connecting channel 310 may be provided between the two separating containers 100, 101. The further channel 310 may also be provided with a check valve Y that may open at higher cracking pressure than that of check valves X, Z. This means that check valve Y may open within a different (higher) centrifugal force range than valves X and Z.

In this example, the connecting channels 300 and 310 may be rigid channels. In alternative examples, flexible connecting channels may be foreseen. Furthermore, in more examples other passive valve systems substantially as hereinbefore described may be foreseen. According to this example, the connecting channels may be respectively connected to the separating and receiving containers at a distal end thereof with respect to the centrifuge rotating axis when in use.

Figure 4A:
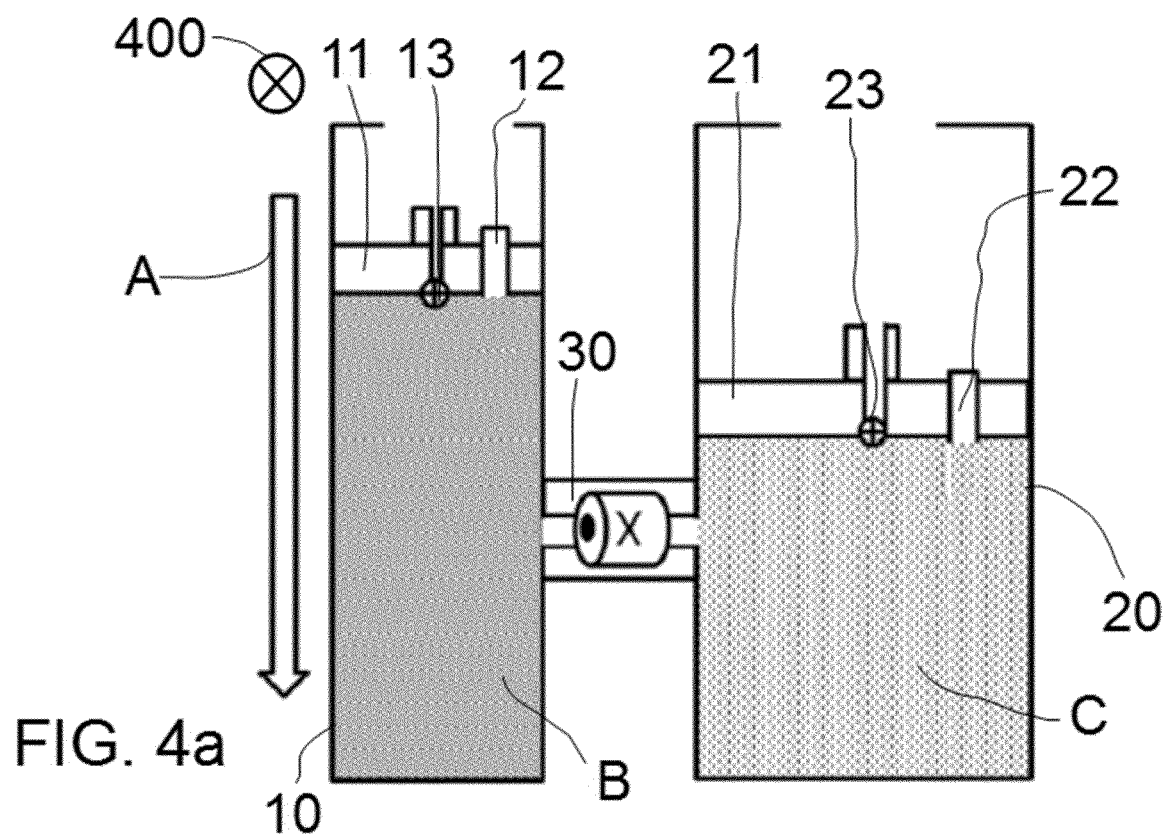
FIGS. 4*a*, 4*b*, 4*c* and 4*d* show an example of a method of obtaining a product by combining phases of a fluid in the device of FIG. 1.
Figure 4B:
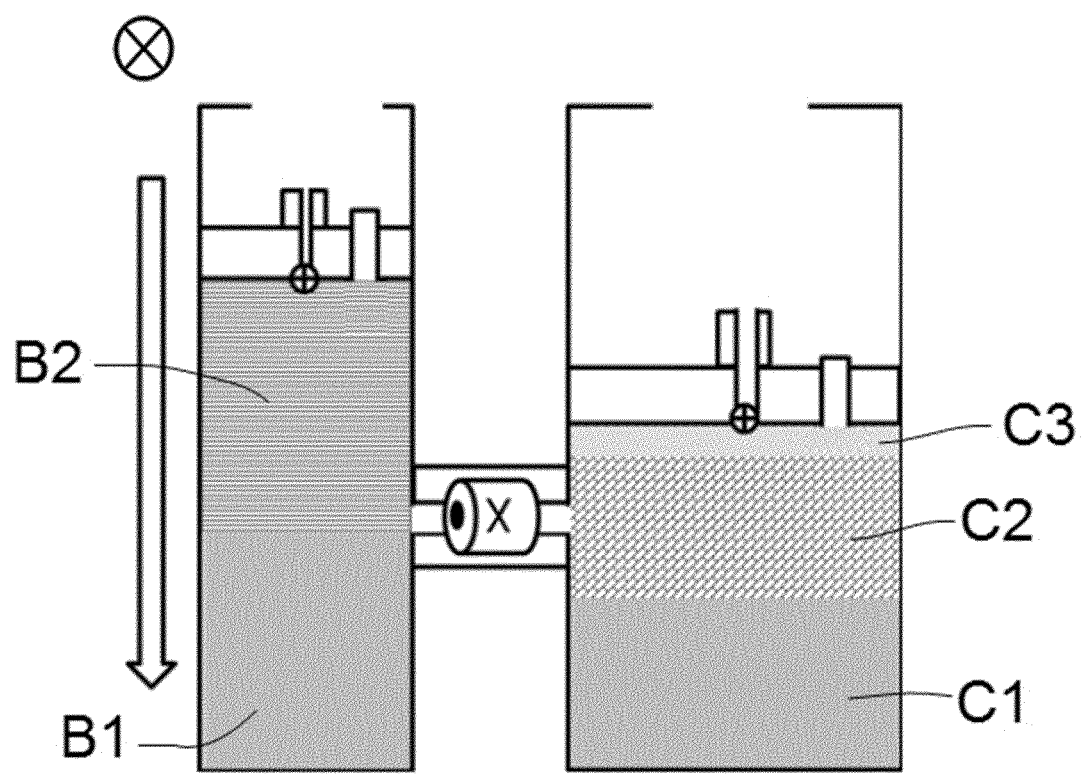
Figure 4C:
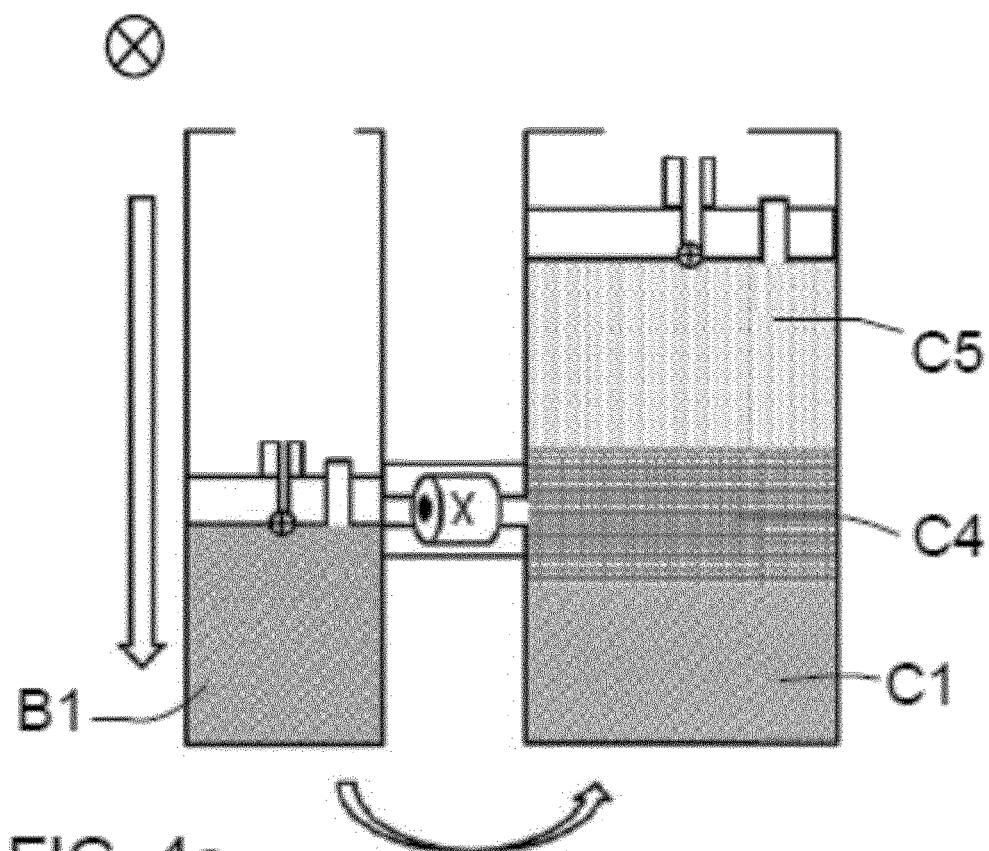
Figure 4D:
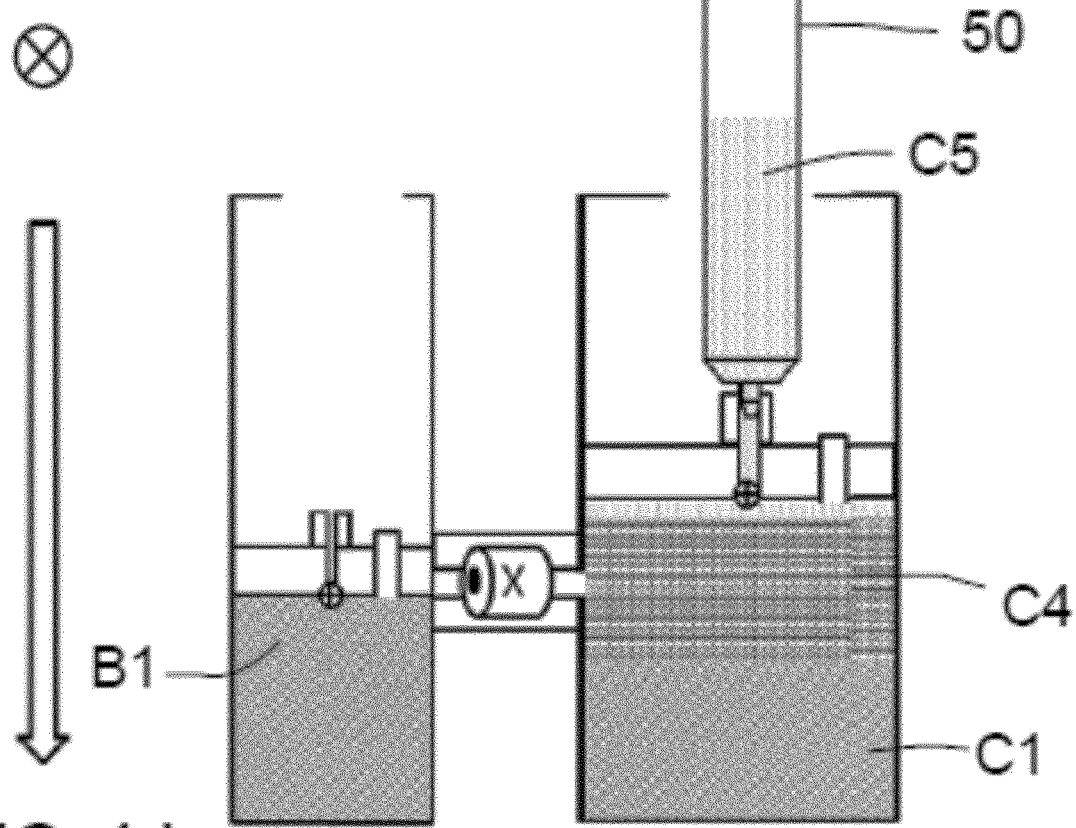

FIGS. 4a-4d show an example of a method of obtaining a product by combining phases of a fluid in the device of FIG. 1. In an example the method may be used for obtaining a cytokine-rich serum by combining phases of blood. Initially the containers 10, 20 may be empty and plungers 11, 21 may be provided at intermediate positions within the containers. The method may comprise the steps of:

filling the separating container 10 with blood and anticoagulant B and the receiving container 20 with blood (without anticoagulant) C;

introducing the device within a centrifuge platform (not shown) such that the containers 10, 20 may be arranged side by side and with their longitudinal axis substantially perpendicular to the rotating axis 400 of the centrifuge, i.e. substantially parallel to a direction of the centrifugal force (arrow A) generated by rotating the centrifuge;

rotating the centrifuge at a first centrifugal speed range able to generate a centrifugal force within 100-600 g during 5-20 minutes so as to separate the fluid B, C within each container 10, 20 (in the example of FIG. 4b, plasma and buffy coat B2 and RBCs B1 may be obtained in the separating container 10 and RBCs C1, a first clot C2 and supernatant C3 may be obtained in the receiving container 20);

continue rotating the centrifuge up to a second centrifugal speed range able to generate a centrifugal force within 400-1000 g that creates the pressure difference able to open check valve X and to transfer a phase B2 of the blood and anticoagulant mixture that is left closer to the rotating axis 400 and which corresponds to Platelet poor plasma (PPP) and platelet rich plasma (PRP) from the separating container 10 to the receiving container 20 and mix it with the blood without anticoagulant C provided within the receiving container (which was separated into a first clot C2 and supernatant C3), continue rotating the centrifuge at a third centrifugal speed range able to generate a centrifugal force within 750-2000 g during 5-20 minutes so as to mix and separate into two phases C4 and C5 the fluid mixture (C2+C3+B2) held within the receiving container 20 as shown in FIG. 4c;

stopping the centrifuge; and extracting from the filling/extracting valve 23 provided in the receiving container 20 a phase C5 that is left closer to the filling/extracting valve 23 (or to the rotating axis 400 when mounted in the centrifuge platform) which corresponds to cytokine-rich serum as shown in FIG. 4d.

In some examples, for the extracting step a sterile syringe may be used. Alternatively, the plunger 21 of the receiving container 20 may be pushed in a direction of a longitudinal axis of the container 20 so as to cause the phase of the fluid mixture that is left closer to the filling/extracting valve 23, to be pushed up into a container 50 that may be disposed in the filling/extracting valve 23.

In some examples, rotating the centrifuge at a first centrifugal speed range able to generate a centrifugal force within 100-600 g during 5-20 minutes may be divided in two stages, namely:

a) rotating the centrifuge at a centrifugal speed able to generate a centrifugal force within 100-300 g so as to separate the blood with anticoagulant B provided in the separating container 10 into buffy coat and plasma B2 and RBCs B1 and the blood C held within the receiving container 20 in RBCs C1, a first clot C2 and a supernatant C3, and b) rotating the centrifuge at a centrifugal speed able to generate a centrifugal force within 200-600 g so as to centrifuge the first clot C2 and the supernatant C3 of the receiving container 20 and arrange the plasma and buffy coat B2 of the separating container in PPP and PRP.

In some examples, overlapping the centrifugal speed ranges may be of interest in order to carry out part of the steps substantially simultaneously and reduce the overall procedure time. For example, for obtaining the cytokine-rich serum an overall procedure time reduction may be obtained by overlapping the step of centrifuging the first clot and the supernatant of the receiving container (step b above) with the step of transferring the PPP and PRP from the separating container to the receiving container.

In some examples, the step of rotating the centrifuge at a third centrifugal speed range able to generate a centrifugal force within 750-2000 g during 5-20 minutes may comprise a first period of high centrifugal force (within 750-2000 g) during around 5-10 minutes, a second period in which the centrifuge is stopped or slowed down to lower speeds able to generate a centrifugal force within 0-100 g during around 1-5 minutes and a further period of around 5-10 minutes rotating at centrifugal speeds able to generate a centrifugal forces within 750-2000 g. In further alternatives, these periods may be repeated depending on circumstances and on e.g. the length of each period.

In more examples the containers 10, 20 may each comprise an air filter 12, 22 as described in connection with FIG. 1. In these cases, as the containers 10, 20 are filled with the fluid, the air filters 12, 22 evacuate sterile air contained therein. In those cases having waterproof air filters (hydrophobic), when the liquid touches the filter, the filter may be saturated thus preventing the passage of liquid therethrough.

Figure 5A:
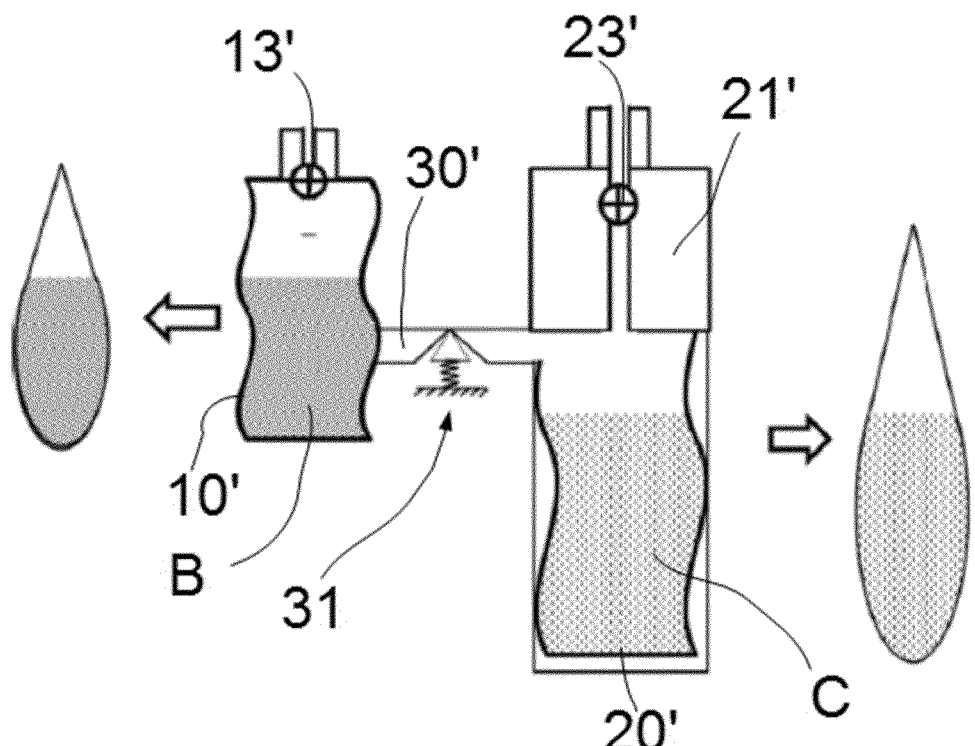
FIGS. 5*a*, 5*b*, 5*c* and 5*d* show an example of a method of obtaining a product by combining phases of a fluid in the device of FIG. 2.
Figure 5B:
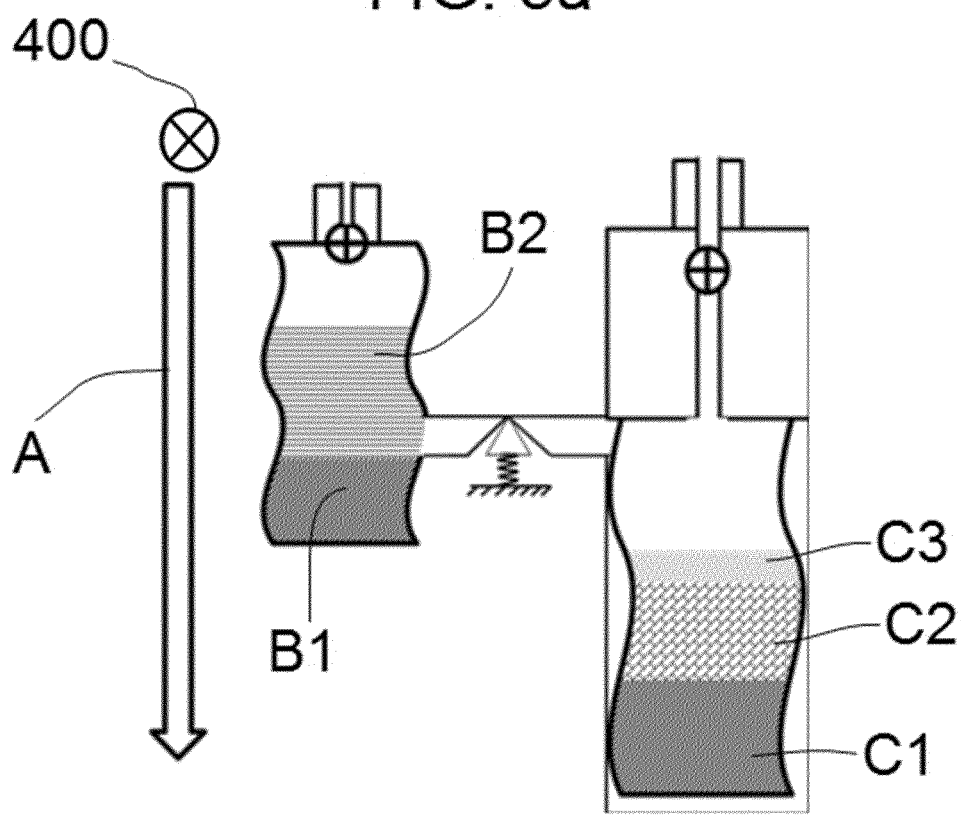
Figure 5C:
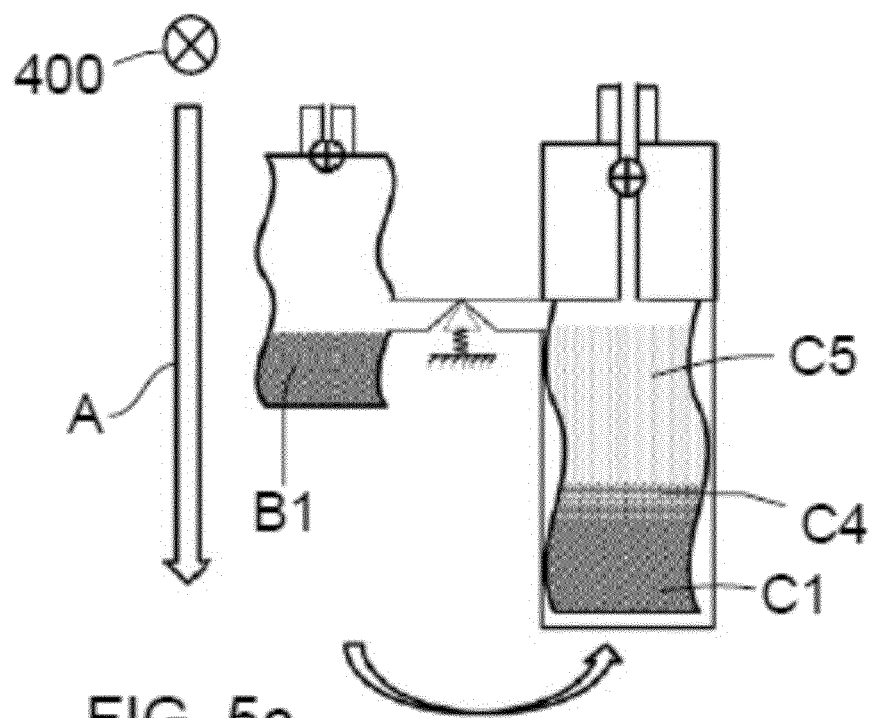
Figure 5D:
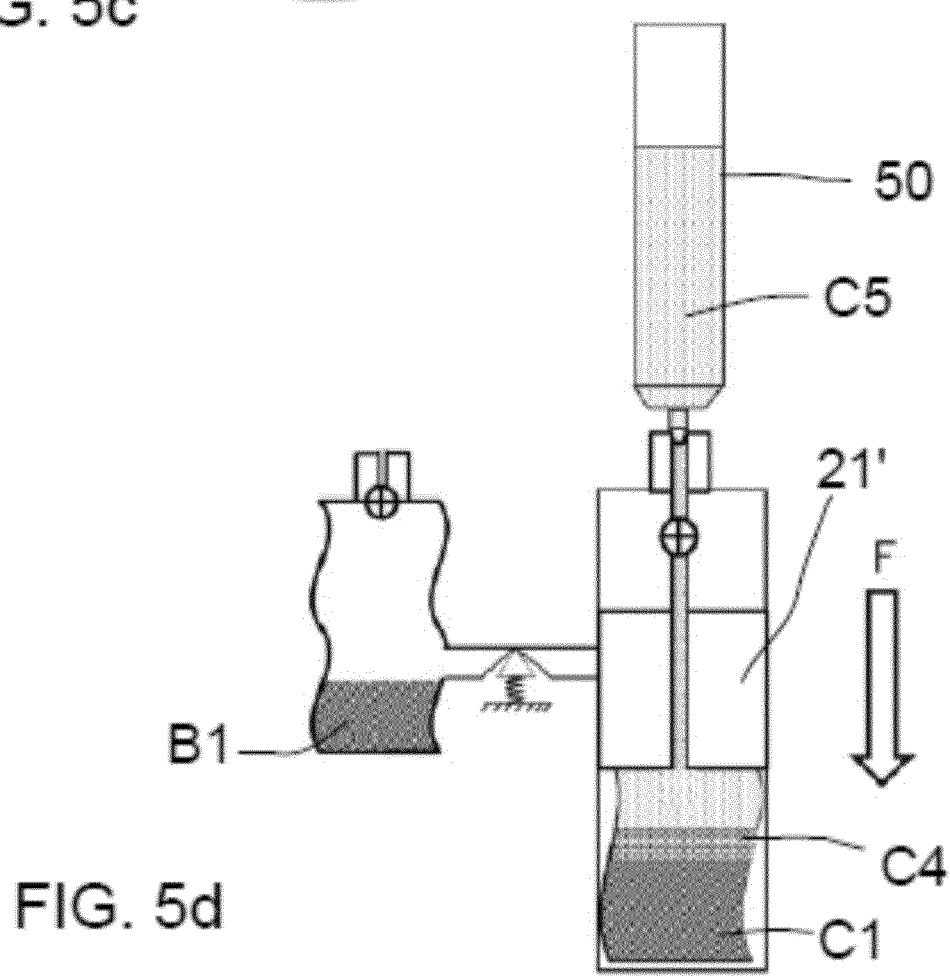

FIGS. 5*a*-5*d* show an example of a method of obtaining a product by combining phases of a fluid in the device of FIG. 2. Initially the containers 10', 20' may be empty. An alternative method for obtaining a cytokine-rich serum by combining phases of blood may be described for the device of FIG. 2. In this example, the method may comprise:

filling the separating container 10' with blood and anticoagulant B and the receiving container 20' with blood (without anticoagulant) C;

introducing the containers 10', 20' within a holder (see FIG. 2) and introducing the holder within a centrifuge platform (not shown) such that the containers 10', 20' may be arranged side by side and with their longitudinal axis substantially perpendicular to the rotating axis 400 of the centrifuge, i.e. substantially parallel to a direction of the centrifugal force (arrow A) generated by rotating the centrifuge;

rotating the centrifuge at a first centrifugal speed range able to generate a centrifugal force within 100-600 g during 5-20 minutes so as to separate the fluid within each container 10', 20' (in the example of FIG. 5*b*, buffy coat and plasma B2 and RBCs B1 may be obtained in the separating container 10' and RBCs C1, a first clot C2 and supernatant C3 in the receiving container 20';

continue rotating the centrifuge up to a second centrifugal speed range able to generate a centrifugal force within 400-1000 g that opens valve 31 and able to transfer a phase B2 of the blood and anticoagulant mixture that is left closer to the rotating axis 400 and which corresponds to PPP and PRP from the separating container 10' to the receiving container 20' and mix it with the blood without anticoagulant C provided within the receiving container 20' (which was separated into a first clot C2 and supernatant C3), continue rotating the centrifuge at a third centrifugal speed range able to generate a centrifugal force within 750-2000 g during 5-20 minutes so as to mix and separate into two phases C4 and C5 the fluid mixture (C2+C3+B2) held within the receiving container 20' as shown in FIG. 5*c*;

stopping the centrifuge; and extracting from the filling/extracting valve 23' provided in the receiving container 20' a phase C5 that is left closer to the filling/extracting valve 23' which corresponds to cytokine-rich serum as shown in FIG. 5*d*.

Similarly to the previous method, in some examples, for the extracting step a sterile syringe may be used. Alternatively, a plunger 21' of the receiving container 20' may be pushed in a direction of a longitudinal axis of the container 20 (see arrow F) so as to cause the fluid, in fact a phase of the fluid mixture that remains closer to the rotating axis when being inserted in the centrifuge platform, to be pushed up through a conduct that may be disposed in the filling/extracting valve 23' as shown in FIG. 5*d*. It should be noted however that this plunger may not act as a weight to aid in creating the pressure difference that opens the valve.

In the example of FIGS. 5*a*-5*d*, rotating the centrifuge at a first centrifugal speed range able to generate a centrifugal force within 100-500 g during 5-20 minutes may also be divided in two stages substantially as described in connection with FIGS. 4*a*-4*d*. And the step of rotating the centrifuge at a third centrifugal speed range able to generate a centrifugal force within 750-2000 g during 5-20 minutes may comprise different periods as explained above in connection with FIGS. 4*a*-4*d*. Alternative, other additional periods substantially as hereinbefore described may be foreseen.

Figures 6A, 6B:
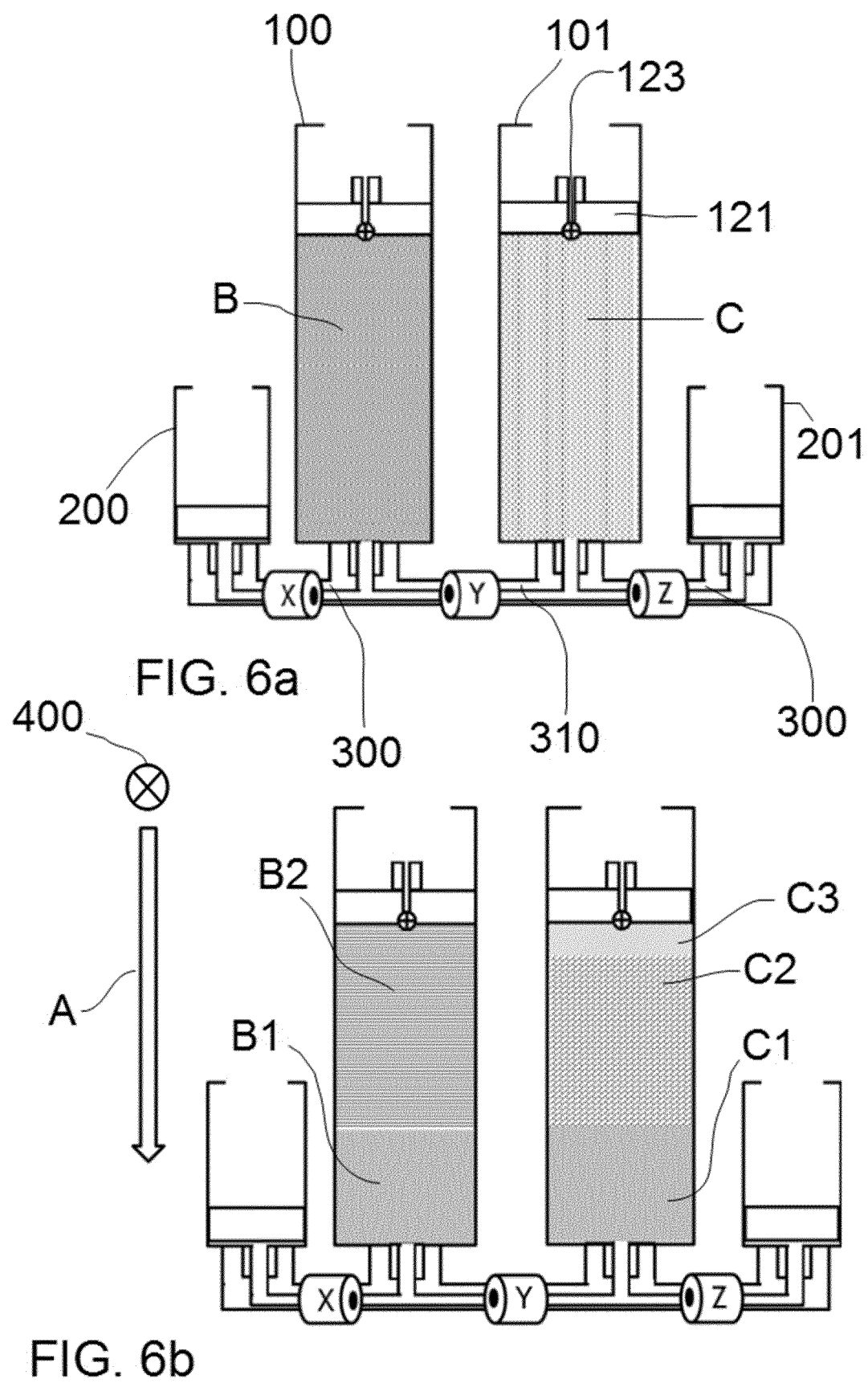
FIGS. 6*a*, 6*b*, 6*c*, 6*d* and 6*e* show an example of a method of obtaining a product by combining phases of a fluid in the device of FIG. 3.
Figure 6C:
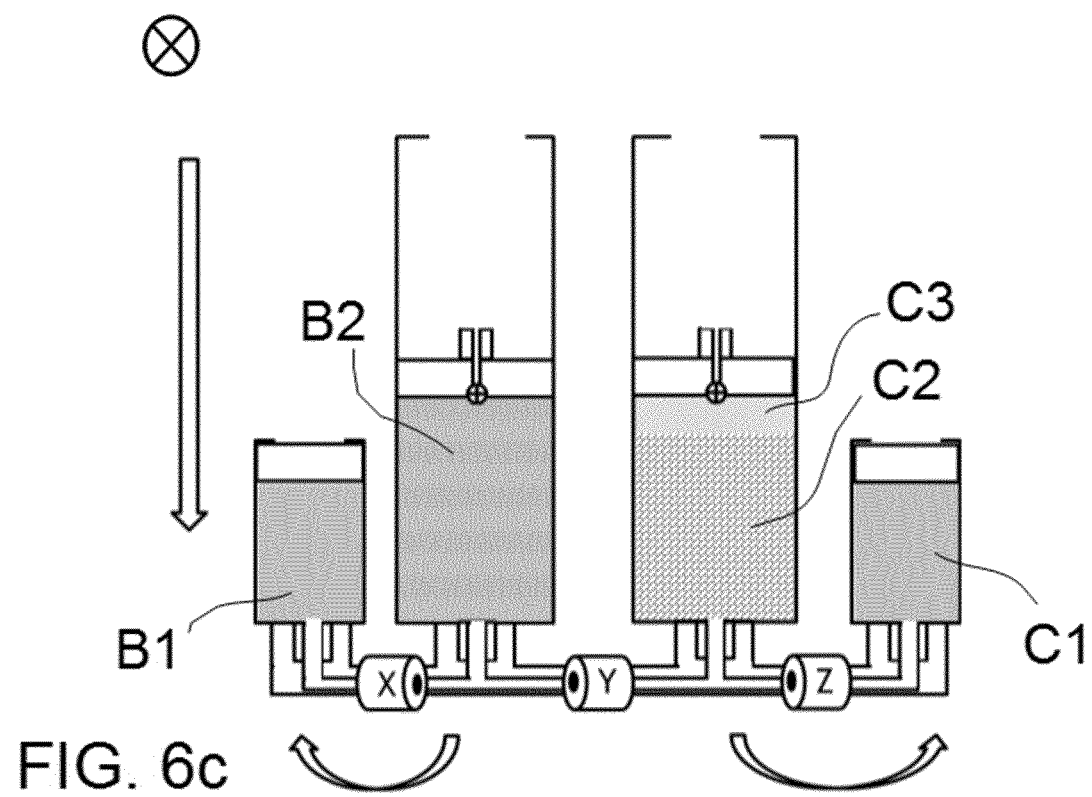
Figure 6D:
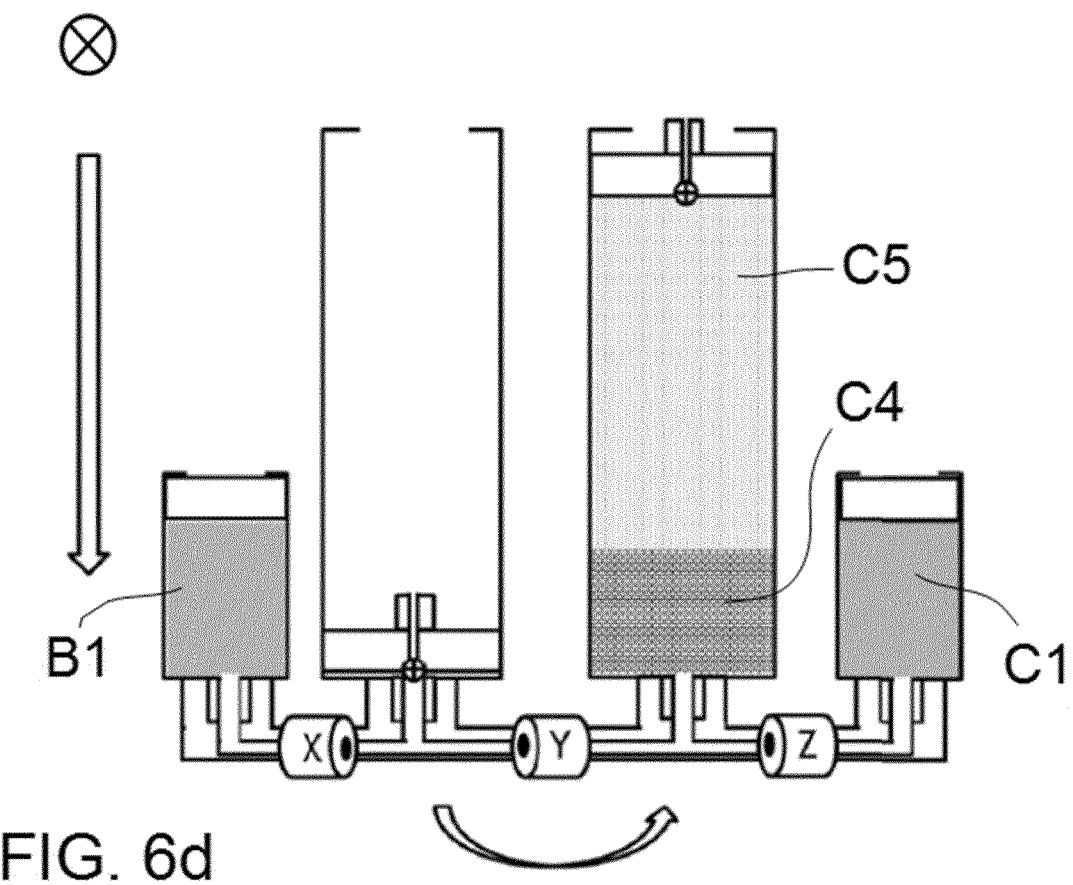
Figure 6E:
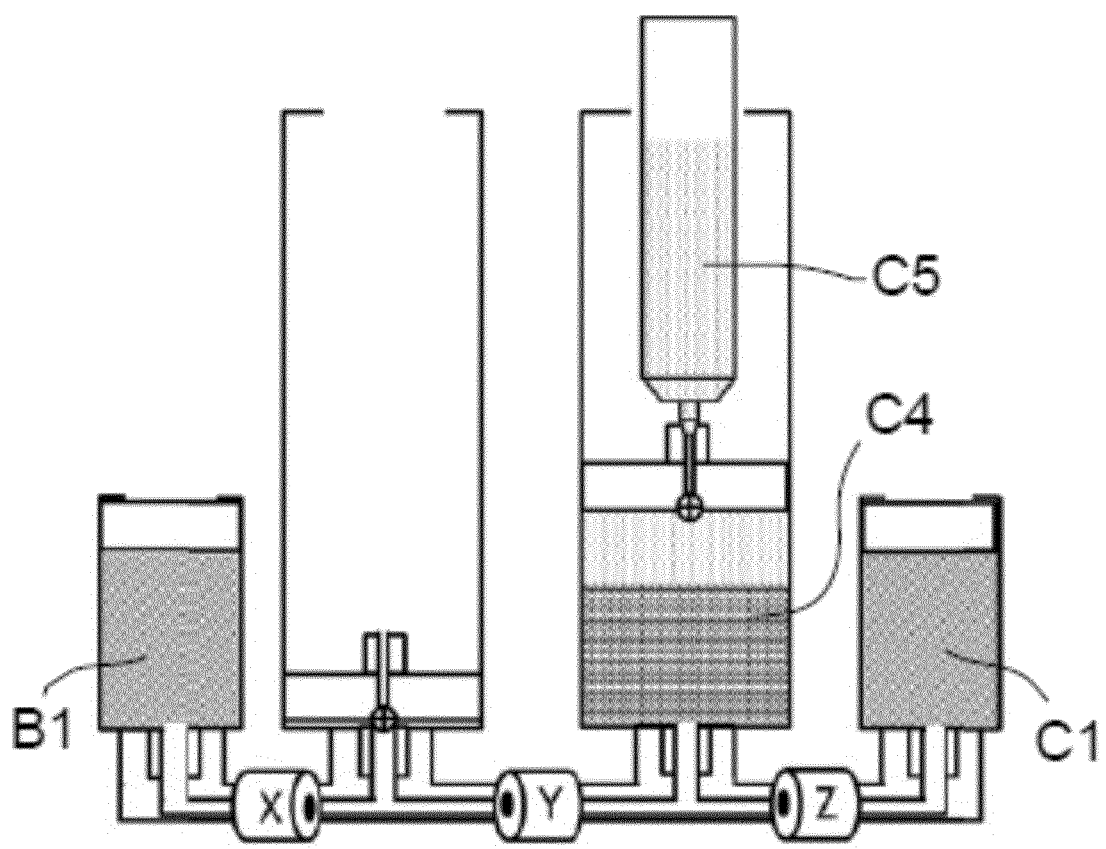

FIGS. 6*a*-6*e* show an example of a method of obtaining a product by combining phases of a fluid in the device of FIG. 3. Initially the containers 100, 101, 200, 201 may be empty. An alternative method for obtaining a cytokine-rich serum by combining phases of blood may be described for the device of FIG. 3. In this example, the method may comprise:

filling the separating container 100 with blood and anticoagulant B and the separating container 101 with blood (without anticoagulant) C;

introducing the containers 100, 101, 200, 201 within a centrifuge platform (not shown) such that the containers may be arranged side by side and with their longitudinal axis substantially perpendicular to the rotating axis 400 of the centrifuge, i.e. substantially parallel to a direction of the centrifugal force (arrow A) generated by rotating the centrifuge;

rotating the centrifuge at a first centrifugal speed range able to generate a centrifugal force within 100-600 g during 5-20 minutes so as to separate the fluid B, C within each separating container 100, 101 (in separating container 100 buffy coat and plasma B2 and RBCs B1 may be obtained and in the separating container 101 RBCs C1, a first clot C2 and supernatant C3 may be obtained as shown in the example of FIG. 6*b*);

continue rotating the centrifuge up to a second centrifugal speed range able to generate a centrifugal force within 300-700 g that creates the pressure difference able to open check valves X, Z and to able transfer a phase B1 and C1 of the fluid mixture that is left more distant to the rotating axis 400 from each separating container 100, 101 to a respective receiving container 200, 201. In this example, RBC's (B1, C1) which have the highest density may be transferred from each separating container 100, 101 to each receiving container 200, 201 as shown in FIG. 6*c*;

continue rotating the centrifuge at a third centrifugal speed range able to generate a centrifugal force within 700-1000 g that creates the pressure difference able to open check valve Y so as to transfer the phase B2 (PPP and PRP) that remains within the separating container 100 to the separating container 101 and mix it with the first clot C2 and supernatant C3 that remains within the separating container 101;

continue rotating the centrifuge at a fourth centrifugal speed range able to generate a centrifugal force within 750-2000 g during 5-20 minutes so as to mix and separate into two phases (second clot C4 and supernatant SN1 C5) the fluid mixture held within the separating container 101 as shown in FIG. 6d;

stopping the centrifuge; and extracting from the filling/extracting valve 123 provided in the separating container 101 a phase C5 that may be left closer to the filling/extracting valve 123 which corresponds to cytokine-rich serum as shown in FIG. 6e.

In some examples, for the extracting step a sterile syringe may be used. Alternatively, the plunger 121 may be pushed along a direction of a longitudinal axis of the container 101 so as to cause the fluid, in fact a phase C5 of the fluid mixture that remains closer to the rotating axis when in use, to be pushed up into a container 50 disposed in the filling/extracting valve 123.

Also in this example, rotating the centrifuge at a first centrifugal speed range able to generate a centrifugal force within 100-600 g during 5-20 minutes may be divided in two stages substantially as described above in connection with FIGS. 4a-4d. And the step of rotating the centrifuge at a fourth centrifugal speed range able to generate a centrifugal force within 750-2000 g during 5-20 minutes may comprise different periods as explained above in connection with FIGS. 4a-4d. Alternative, other additional periods substantially as hereinbefore described may be foreseen.

Figure 7A:
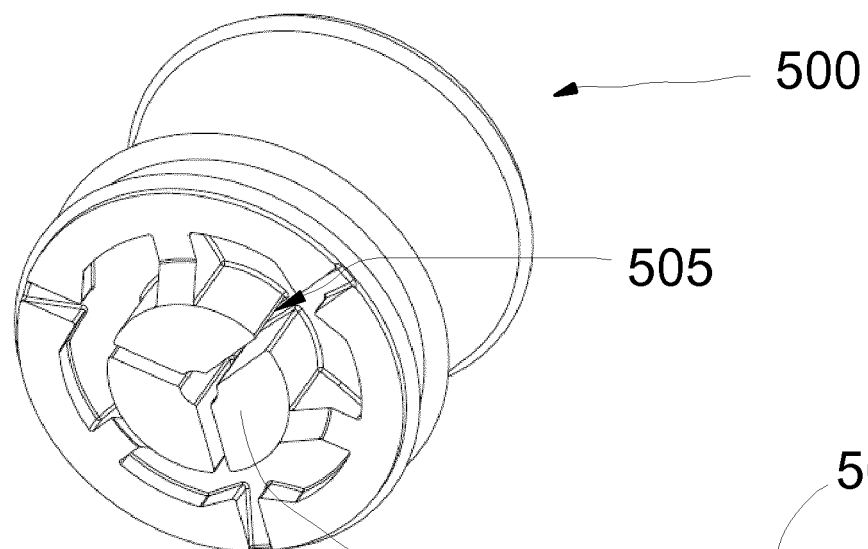
FIGS. 7*a*, 7*b* and 7*c* show an example of a plunger that may be used in any of the examples of the device.
Figure 7B:
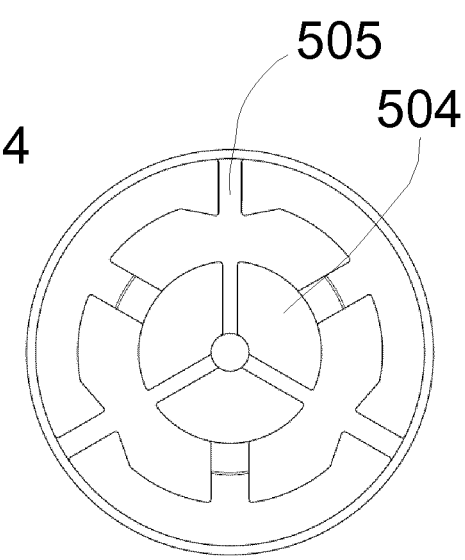
Figure 7C:
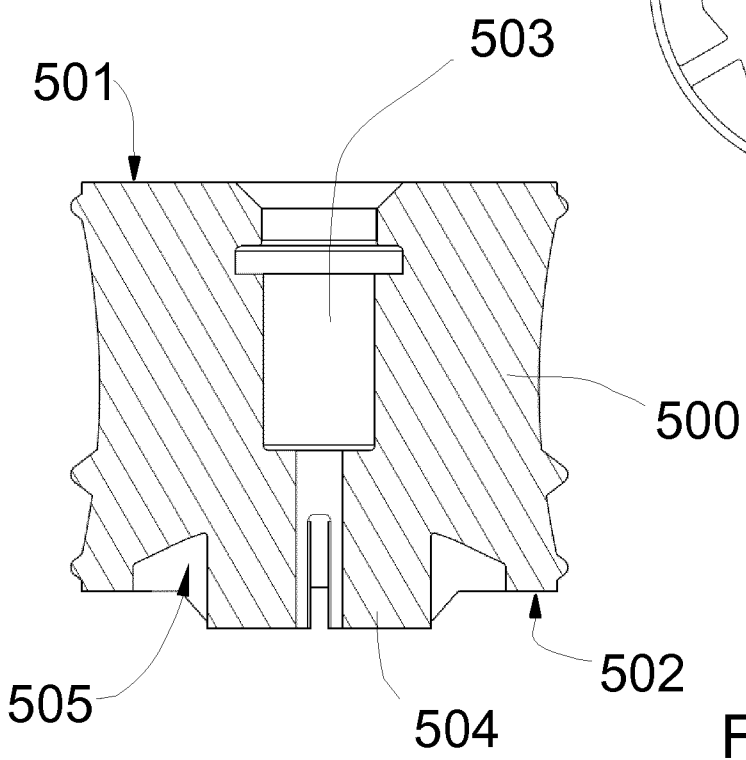

FIGS. 7a-7c show an example of plunger 500 that may be used in any of the examples substantially as hereinbefore described. FIG. 7a shows a perspective, FIG. 7b a bottom view and FIG. 7c a cross-sectional view. The Inventors have found that this type of plunger may particularly be interesting for replacing plungers 21, 21' and 101 described in connection with above examples.

In the example of FIGS. 7a-7c the plunger 500 may extend from an outside end 501 to an inside end 502. The inside end 502 in use faces an inside of the container on which the plunger is mounted, e.g. containers 20, 20' or 101 described in the examples above. As explained in connection with plungers 21, 21' and/or 101', the plunger 500 may also comprise a filling and extracting valve 503. In a similar manner as explained in connection with FIG. 4d, 5d or 6e, extracting of the final product may thus be done through the filling and extracting valve 503 by pushing the plunger 500 in a direction of a longitudinal axis of the container so as to cause the fluid held in the container 21, 21' or 101 to be pushed up into a further container 50 that may be connected at the filling and extracting valve 503.

In some examples, the inside end 502 of the plunger 500 may be provided with one or more projections 504 and/or grooves 505 or combinations thereof. In the example shown in FIGS. 7a and 7b three projections are provided with channels/grooves in between them. However, other number of projections and channels or grooves there between may be foreseen. This way, when the plunger 500 is moved downwards, i.e. pushed towards the fluid held in the container in which the plunger is mounted (as shown e.g. by arrow F of FIG. 5d), the protrusions 504 may squeeze the fluid further. A portion of the fluid phase that is to be extracted and that may be mixed with the next phase, particularly when the next phase is solid or semi-solid, can be squeezed further from this immediately next phase thus increasing the amount of fluid of the phase that is to be extracted that may be obtained.

In the example of FIGS. 4a-4d if plunger 21 is replaced with a plunger 500 substantially as explained in connection with FIGS. 7a-7c, then the performance of the step of extracting from the filling/extracting valve 23 provided in the receiving container 20 a phase C5 that is left closer to the filling/extracting valve 23 (or to the rotating axis 400 when mounted in the centrifuge platform) which corresponds to cytokine-rich serum as shown in FIG. 4d can be increased by squeezing on to phase C4 (in above examples being a fibrin gel, i.e. a gelatinous mass) with the projections 504 of the plunger 500 (provided plunger 500 has replaced plunger 21) so as to extract further fluid in phase C5 that may be left mixed with fluid in phase C4 that is a clot (i.e. a fibrin gel). An increased performance means that more fluid in phase C5 can be obtained.

A substantially similar analysis may be made with the example of FIGS. 5a-5d if plunger 21' is replaced with a plunger 500 substantially as explained in connection with FIGS. 7a-7c or with the example of FIGS. 6a-6d if plunger 101 is replaced with a plunger 500 substantially as explained in connection with FIGS. 7a-7c.

In some examples in which the connecting channels may be coupled to the containers at their distal ends with respect to the centrifuge rotating axis, the connecting channels and the valve systems may be arranged together inside a housing having four connecting ports, one for each container. In some of these cases, the separating connecting channel may further be arranged in the housing. And the valve systems may further be provided inside the housing.

In some of the examples described above, the volume of the phase of fluid to be transferred to the receiving container may be controlled by properly selecting the size, i.e. volume, of the receiving container and/or by properly selecting a relative position of containers with respect to the rotating axis of the centrifuge.

In some examples, a method for separating and transferring components of an isolated liquid biological sample (e.g. blood) may comprise:

a) submitting an isolated biological sample comprising platelets and/or leukocytes to a centrifugal force comprised from 100 g to 200 g to obtain a first clot (C2 in the figures) and a supernatant (C3 in the figures); and b) submitting only the clot (C2), or alternatively the clot (C2) and supernatant (C3) of step (a) to a centrifugal force applied with the following centrifugation pattern:

(i) first centrifuging the clot of step (a), or alternatively the clot and supernatant, at a centrifugal force comprised from 400 g to 500 g, more particularly at 400 g;

(ii) increasing the centrifugal force applied in step (i) up to a centrifugal force comprised from 800 g to 1000 g, while adding a composition (B2 in the figures) comprising fibrinogen, platelets and/or leukocytes selected from the group consisting of a platelet rich plasma (PRP), a platelet concentrate, a leukocyte-rich plasma, a leukocyte concentrate, a platelet poor plasma (PPP), a plasma concentrate and mixtures or combinations thereof, to obtain a second clot (C4 in the figures), which is a fibrin gel composition comprising platelets and/or leukocytes embedded in a fibrin matrix, said gel comprising also a serum with cytokines and coagulation factors in liquid form disposed in-between the fibrin matrix;

(iii) optionally increasing the centrifugal force applied in step (ii) up to a centrifugal force comprised from 1000 g to 1500 g to break the fibrin matrix and to obtain a supernatant SN1 (C5 in the figures), which is a serum comprising cytokines and coagulation factors; and (iv) optionally, recovering the supernatant SN1 (C5).

With this centrifugation pattern (continuous increasing of centrifugal force), separation of supernatant with cytokines and/or growth factors may be produced with minimal recovering and manipulation steps. In the particular case when the biological sample comprising platelets and/or leukocytes is blood, the serum obtained in the centrifugation at a centrifugal force comprised from 400 g to 500 g, acts as source of thrombin (coagulation factor) and of a specified pattern of cytokines that activate the cellular elements of the composition comprising fibrinogen, platelets and/or leukocytes.

In some examples, prior to step (a) ionic calcium may be added e.g. by adding $CaCl_2$ and adjusted to a final concentration from 1.0 μmol/ml to 50.0 μmol/ml and pH of the final solution may be adjusted to a pH comprised from 7.0 to 7.6, by adding an ionic calcium source to the recovered supernatant and, optionally, a pH adjusting agent. This source of calcium added to promote clotting may also act further as chemical mediator or activator of the cells that can be contained in the isolated biological sample comprising platelets and/or leukocytes. Adjustment of ionic calcium may be performed by addition to the biological sample by means of a pipette, or alternatively, the calcium chloride may be present in the recipient (tube) where the biological sample is collected. In another example, the ionic calcium source may be added after step (b) to a final concentration from 1.0 μmol/ml to 50.0 μmol/ml in the mixture, particularly to a final concentration of 24 μmol/ml. An example of source is a $CaCl_2$ solution at 10% w/w (4 mg/ml). However, any source of calcium would also be useful as above indicated.

In some examples, a PRP may be added in step (b)(ii).

In another example, wherein the centrifugal force in step (b) may be applied by means of an increasing centrifugation gradient and with the above-disclosed pattern, centrifugations of (i) and (ii) may be performed for a time from 1 to 2 minutes and centrifugation of (iii) for a time from 4 to 6 minutes, particularly 6 minutes.

In some examples, wherein the centrifugal force in step (b) may be applied by means of an increasing centrifugation gradient and with the above-disclosed pattern, the isolated biological sample may comprise platelets and/or leukocytes is preferably whole blood with or without anticoagulant agents. In particular, the sample may be whole blood in the absence of anticoagulants. When whole blood is used as biological sample, and centrifugal force is applied, a layer of RBC is formed generally at the bottom of the recipient where blood is collected, since this is the fraction of blood with a higher density. In this example, when whole blood (with or without anticoagulants) is used, the method may further comprise a step of totally or partially removing RBC of the isolated biological sample as explained in connection with FIGS. 6a-6e above.

Isolation of all (totally) or part (partially) of RBC may in particular be performed after the first clot and supernatant of step (a) are formed, more in particular simultaneously during step (b), and most in particular during the first centrifuging (i) of the clot of step (a), or alternatively of the clot and supernatant of (a), and at a centrifugal force comprised from 400 g to 500 g.

Throughout the present description and claims "totally removing" is to be understood that all or mostly of the RBC are removed. For "partially removing" is to be understood that only ½ or ¾ parts of the erythrocytes are removed.

Furthermore, the method may be carried out at a temperature comprised from 18° C. to 40° C. In particular at 37° C., thus mimicking the physiological conditions. The control of the temperature assures that no degradation of the obtained product takes place.

With this method for separating and transferring components (phases) of a fluid, e.g. an isolated liquid biological sample, in which step (b) may include adding a composition comprising fibrinogen, platelets and/or leukocytes while applying the centrifugal force for the strong activation of platelets and/or leukocytes in the biological sample, a simplified method for separation may be achieved that avoids multi-steps, external manipulation and extra energy for actuating on opening/closing valve systems.

With the method disclosed above and when whole blood without anticoagulants is used as isolated biological sample, it can be obtained a serum comprising cytokines and coagulation factors, said serum being enriched in cytokines in relation to a serum obtained in an ordinary way by simply letting clot the whole blood without anticoagulants.

Thus, in some examples a serum obtainable by the methods disclosed above from a whole blood sample without anticoagulants may further be provided. This serum so obtained and defined may be used as an active ingredient in a pharmaceutical composition. Therefore, a pharmaceutical composition comprising an effective amount of the serum as defined above, together with pharmaceutically acceptable carriers and/or excipients may be provided.

In an example of the method, step (b) may be stopped in (ii), and then a fibrin gel composition comprising platelets and/or leukocytes embedded in a fibrin matrix may be obtained, said gel comprising also a serum with cytokines and coagulation factors in liquid form disposed in-between the fibrin matrix. This fibrin gel composition can also be the active ingredient of a pharmaceutical composition together with pharmaceutically acceptable carriers and/or excipients.

All these serums and fibrin gel compositions, or pharmaceutical compositions comprising them, may be used as drugs. Particularly, they are for use in the treatment of a disease or pathology selected from the group consisting of an inflammatory pathology, a degenerative disease, a disease caused by ischemia, a vascular disease, an immunological pathological process, and trauma. Alternatively, they are for use as an organ and/or tissue regenerative and/or reparative agent.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc., must also be "acceptable" in the sense of being compatible with the other ingredients of the formulation. Suitable carriers, excipients, etc. can be found in standard pharmaceutical texts, and include, as a way of example preservatives, agglutinants, humectants, emollients, and antioxidants.

The term "effective amount" as used herein, means an amount of an active agent high enough to deliver the desired benefit (either the treatment or prevention of the illness), but low enough to avoid serious side effects within the scope of medical judgment.

The term "fibrin" as used herein, refers to a fibrillar protein with the ability to form three dimensional networks. This protein plays an important role in the coagulation process in view of its properties. It has the structure of a pole with three globular areas. It has the ability to create aggregates with other molecules forming a soft clot. Not normally found in the blood, it is formed from circulating fibrinogen, which by the action of the enzyme called thrombin is converted to fibrin, which has coagulant effects.

For "anticoagulant" is to be encompassed in the sense of this description, as an endogenous or exogenous substance that interferes with or inhibits blood clotting. Non-limiting examples of anticoagulants are the activators of antithrombin III and heparin, low molecular weight ardeparin, certoparin, nadroparin, logiparin, parnaparin, reviparin and tedelparina and recombinant antithrombin III, tissue factor inhibitor (TF)-Factor VIIa such as TF mutants, anti-TF antibodies, inhibitors of factor VII, thrombin inhibitors such as antistatin factor Xa inhibitors, TAP (tick anticoagulant peptide), DX9065, lefaxin, fondaparinux, terostatin, YM-75466 and ZK-807,834, antibodies against factor IXa and Xa, activators of protein C pathway and selective inhibitors of thrombin as argatroban, bivalirudin, efegatran, H376/95, hirugen, inogatran, melagatran, napsagatrán, UK-156406 and ximelagatran, and chemical compounds that capture calcium ions, such as ethylenediaminetetraacetic acid (EDTA), citrate (usually sodium citrate) and oxalate.

In some examples, the anticoagulant may be sodium citrate e.g. trisodium citrate $Na_3C_6H_5O_7$ with a concentration of around 3.2% and in a ratio of 1:9, or what is the same e.g. for each 9 ml of blood 1 ml of anticoagulant may be used.

Example 1

Preparation of Cytokine-Rich Serum or Serum Rich in Cytokines (SRC, Also Named SN1):

A blood sample without anticoagulant and with 15 μmol/ml of $CaCl_2$ (10%), was collected in a collection tube. Then it was centrifuged such that a centrifugal force of substantially 200 g is obtained for 10 minutes at room temperature to form a clot (platelets and leukocytes with erythrocytes) at the bottom and a supernatant (serum). The clot and supernatant were further centrifuged at 400 g for 2 minutes. This allowed initiating strong activation of platelets and/or leukocytes, and at the same time the removal of RBC that were eluted from the bottom of the collection tube through a duct comprising a valve with a cracking pressure calibrated at a centrifugal force from 400 g to 500 g. After this step at 400 g, the centrifugal force was raised up to 1000 g for 2 minutes. Meanwhile centrifugal force was of 1000 g, it was automatically added a platelet-rich plasma (PRP) to the clot and supernatant of the tube. Addition of PRP was performed by means of a duct connecting the tube with a container comprising the PRP, said duct provided with a valve with a cracking pressure calibrated at a gravity force from 800 g to 1000 g, in such a form that PRP was displaced from its original container to the tube with the clot and supernatant. Mixture of PRP with the clot and supernatant allowed obtaining a second clot, which was a fibrin gel composition comprising platelets and/or leukocytes embedded in a fibrin matrix, said gel comprising also a serum with cytokines and coagulation factors in liquid form disposed in-between the fibrin matrix.

In order to recover the serum with cytokines and coagulation factors (SN1) the fibrin matrix was broken by further raising gravity force in the rotor up to 1500 g for 6 minutes. 2 ml of this final supernatant (SN1) were extracted for analysis of cytokines and growth factors.

Next table shows an example of the qualitative and quantitative analysis from the supernatants so obtained:

|  | SN1 |
|---|---|
| initial platelet Media 268.6 × 10^9/L |  |
| initial WBC Media 8.6 × 10^9/L |  |
| Platelets Product × 10^9/L | 67.2 |
| Leukocyte Product × 10^9/L | 0.48 |
| TGF-β1 ng/mL | 132.2 |
| FGF - pg/mL | 0.06 |
| IGF-1 ng/mL | 277 |
| HGF - ng/mL | 28.4 |
| EGF - pg/ml | 110.4 |
| VEGF - pg/ml | 578.7 |
| IL-1 β - pg/ml | 8.7 |
| IL-6 - pg/ml | 5.4 |
| IL-8 - pg/ml | 3.4 |
| TNF-α - pg/ml | 4.5 |
| IL-10 - pg/ml | 7.2 |
| PDGF - ng/mL | 158.7 |
| BMP - pg/ml | 30.1 |
| Fibrinogen -g/l | Not detectable |
| Thrombin - U/ml | 80 nM |
|  | 40 U/ml |
| Factor VII - U/dl | 276.2 |
| Von Willebrand Factor - U/dl | 228 |

This final supernatant SN1 was thus obtained with a method comprising (a) submitting an isolated biological sample comprising platelets and/or leukocytes to a centrifugal force comprised from 100 g to 200 g to obtain a first clot and a supernatant; and (b) submitting the clot and supernatant of step (a) to a centrifugal force with a particular pattern of centrifugation with an increasing gradient of centrifugal force, said pattern including: (i) first centrifuging the clot and supernatant, at a centrifugal force comprised from 400 g to 500 g; (ii) increasing the centrifugal force applied in step (i) up to a centrifugal force comprised from 800 g to 1000 g, while it was added a composition comprising fibrinogen, platelets and/or leukocytes selected from the group consisting of a platelet-rich plasma, a platelet concentrate, a leukocyte-rich plasma, a leukocyte concentrate, a platelet-poor plasma, a plasma concentrate and mixtures or combinations thereof. This allowed obtaining a second clot, which was a fibrin gel composition comprising platelets and/or leukocytes embedded in a fibrin matrix, said gel comprising also a serum with cytokines and coagulation factors in liquid form disposed in-between the fibrin matrix. Next, step (b) included a further sub-step of (iii) increasing the centrifugal force applied in step (ii) up to a centrifugal force comprised from 1000 g to 1500 g to break the fibrin matrix and, finally, to obtain the supernatant SN1.

Although the examples provided disclose devices suitable for blood, the present disclosure may further be used for separating and transferring phases of other fluids or biological fluids having different densities such as bone marrow or umbilical cord or placental amniotic fluid.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A system for separating and transferring phases of a fluid through centrifugation comprising:
a centrifuge having a rotating axis,
a centrifuge platform that is rotatable around the rotating axis; and
a device for separating and transferring the phases of the fluid, wherein the device comprises:
a separating container having a receiving end configured to receive the fluid,
a receiving container arranged in fluid communication with the separating container through a connecting channel, and
a passive valve system provided in the connecting channel,
wherein the device is mounted in the centrifuge platform with the separating container and the receiving container arranged side by side and with a longitudinal axis of each container substantially perpendicular to the rotating axis of the centrifuge such that in use at a first predefined range of centrifugal force a fluid provided within the separating container is separated into phases and at a second predefined range of centrifugal force the passive valve system opens, thereby transferring a phase of the fluid from the separating container to the receiving container, and
wherein the connecting channel is coupled to the separating container at a point such that 30-50% of a total volume of the separating container is left more distant from the centrifuge rotating axis than the channel itself such that in use, when the second predefined range of centrifugal force is reached, a phase of the fluid being left closer to the centrifuge rotating axis than the channel flows through the channel to the receiving container.

2. The system of claim 1, wherein the separating container is rigid.

3. The system of claim 1, wherein the receiving container is rigid.

4. The system of claim 1, wherein the separating container and the receiving container are flexible bags and the device further comprises a rigid holder configured to receive the containers and the connecting channel.

5. The system of claim 1, wherein the receiving container comprises a plunger to isolate an inside of the receiving container from the outside, the plunger being reciprocally lengthwise movable in the receiving container, in a direction of the centrifugal force generated in use by rotation of the centrifuge platform and the plunger comprising a filling and extracting valve.

6. The system of claim 5, wherein the plunger extends from an outside end to an inside end, wherein the inside end in use faces the inside of the container and is provided with one or more projections and/or grooves.

7. The system of claim 1, wherein the separating container further comprises a weight at the receiving end, the weight being displaceable in a direction of the centrifugal force generated in use by rotation of the centrifuge platform.

8. The system of claim 7, wherein the receiving container comprises another displaceable weight.

9. The system of claim 1, wherein the separating container is mounted in the centrifuge platform at a different distance to the rotating axis than the receiving container, thereby contributing to create a pressure difference at the passive valve system.

10. A device comprising:
a separating container having a receiving end configured to receive the fluid,
a receiving container arranged in fluid communication with the separating container through a connecting channel, and
a passive valve system provided in the connecting channel,
wherein the device is configured to be mounted in a centrifuge platform with the separating container and the receiving container arranged side by side and with a longitudinal axis of each container substantially perpendicular to a centrifuge rotating axis such that in use at a first predefined centrifugal force range a fluid provided within the separating container is separated into phases and at a second predefined centrifugal force range the passive valve system opens thereby transferring a phase of the fluid from the separating container to the receiving container, and wherein the connecting channel is coupled to the separating container at a point such that 30-50% of a total volume of the separating container is left more distant from the centrifuge rotating axis than the channel itself such that in use, when the second predefined range of centrifugal force is reached and the valve system is opened, a phase of the fluid being left closer to the centrifuge rotating axis than the channel is transferred from the separating container to the receiving container through the channel.

11. A method of obtaining a product made of combining phases of a fluid using a system according to claim 1, the method comprising:
filling the separating container with a fluid,
filling the receiving container with a fluid,
introducing the containers into the centrifuge, rotating the centrifuge platform at a first centrifugal speed range so as to obtain the first predefined centrifugal force range and during a first period of time to perform separation into phases of a fluid provided within the containers,
rotating the centrifuge platform at a second centrifugal speed range so as to reach the second predefined centrifugal force range causing the valve system to open, thereby transferring a phase of the fluid from the separating container to the receiving container,
rotating the centrifuge platform at a third centrifugal speed range so as to obtain a third centrifugal force range and during a second period of time so as to obtain separation into two phases of a fluid mixture housed in the receiving container,
stopping the rotating of the centrifuge platform, and
extracting a product made of combining phases of the fluid mixture housed in the receiving container that is consolidated at a layer closest to the centrifuge rotating axis.

12. The method of claim 11, wherein the receiving container comprises a plunger reciprocally lengthwise movable inside the receiving container, in a direction of the centrifugal force generated in use by rotation of the centrifuge platform, the plunger comprising a filling and extracting valve and extending from an outside end to an inside end, wherein the inside end in use faces the inside of the receiving container, the inside end being provided with one or more projections and/or grooves and the method further comprising
extracting the product made of combining phases of the fluid mixture housed in the receiving container that is consolidated at a layer closest to the centrifuge rotating axis by pushing the fluid mixture with the plunger.

13. The device of claim 10, wherein the receiving container comprises a plunger to isolate an inside of the receiving container from the outside, the plunger comprising a filling and extracting valve and being reciprocally lengthwise movable in the receiving container in a direction of a centrifugal force generated in use by rotation of the platform.

14. The device of claim 13, wherein the plunger extends from an outside end to an inside end of the receiving container, wherein the inside end in use faces the inside of the receiving container and is provided with one or more projections and/or grooves.

* * * * *